United States Patent
Prokopi

(10) Patent No.: US 12,133,860 B2
(45) Date of Patent: Nov. 5, 2024

(54) MICRORNA-BASED THERAPY TARGETED AGAINST LCP-1 POSITIVE CANCERS

(71) Applicant: THERAMIR LTD, Limassol (CY)

(72) Inventor: Marianna Prokopi, Limassol (CY)

(73) Assignee: Theramir Limited, Limassol (CY)

( * ) Notice: Subject to any disclaimer, the term of this patent is extended or adjusted under 35 U.S.C. 154(b) by 170 days.

(21) Appl. No.: 17/266,069

(22) PCT Filed: Aug. 8, 2019

(86) PCT No.: PCT/EP2019/071341
§ 371 (c)(1),
(2) Date: Feb. 4, 2021

(87) PCT Pub. No.: WO2020/030750
PCT Pub. Date: Feb. 13, 2020

(65) Prior Publication Data
US 2021/0369760 A1 Dec. 2, 2021

(30) Foreign Application Priority Data
Aug. 8, 2018 (EP) .................... 18020374

(51) Int. Cl.
*A61P 35/00* (2006.01)
*A61K 31/7105* (2006.01)
(Continued)

(52) U.S. Cl.
CPC .......... *A61K 31/7105* (2013.01); *A61K 45/06* (2013.01); *A61P 35/00* (2018.01); *C12N 15/1135* (2013.01)

(58) Field of Classification Search
CPC ..... A61K 31/7105; A61K 45/06; A61P 35/00; C12N 15/1135; C12N 2310/141; C12N 15/90; C12Q 1/68; C12Q 2600/158
See application file for complete search history.

(56) References Cited

U.S. PATENT DOCUMENTS

2014/0147454 A1* 5/2014 Chakraborty .......... A61K 39/00
536/23.1
2014/0200261 A1 7/2014 Hoge et al.

FOREIGN PATENT DOCUMENTS

WO 2011029903 A1 3/2011
WO 2013048734 A1 4/2013
(Continued)

OTHER PUBLICATIONS

Vesiclepedia database (http://microvesicles.org/) Accessed Mar. 1, 2023 (Year: 2012).*
(Continued)

*Primary Examiner* — Kimberly Chong
*Assistant Examiner* — Ruth Sophia Arieti
(74) *Attorney, Agent, or Firm* — Patent Law Works LLP

(57) ABSTRACT

The present invention relates to a panel of miRNAs comprising miR-16-5p, miR-23a-5p, miR-125b-5p, miR-145-5p, miR-146a-3p, miR-181c-5p, miR-218-5p, miR-495-3p, let-7b-5p, and further comprising one or more miRNAs selected from the group consisting of miR-30a-5p, miR-30b-5p, miR-30c-5p, miR-30d-5p, miR-30e-5p, miR-194-5p, miR-302a-3p, miR-302a-5p, miR-335-3p, miR-335-5p, miR-367-3p, miR-373-3p, and miR-885-5p, and to extracellular vesicles (EVs), e.g. of stem cell origin, loaded with the panel of miRNAs. The present invention further provides the panel or EVs for use in a method of treating LCP-1 positive cancer in a patient.

9 Claims, 6 Drawing Sheets
Specification includes a Sequence Listing.

(51) Int. Cl.
*A61K 45/06* (2006.01)
*C12N 15/113* (2010.01)

(56) References Cited

FOREIGN PATENT DOCUMENTS

| WO | WO-2014125277 A1 | * | 8/2014 | ......... | A61K 31/7105 |
| WO | WO-2016166600 A1 | * | 10/2016 | ......... | A61K 31/7105 |
| WO | 2017005773 A1 | | 1/2017 | | |

OTHER PUBLICATIONS

Kalra et al. 2012. Vesiclepedia: A compendium for extracellular vesicles with continuous community annotation. PLoS Biology. 12: e1001450 (Year: 2012).*
Wu et al 2013 Microvesicles Derived from Human Umbilical Cord Wharton's Jelly Mesenchymal Stem Cells Attenuate Bladder Tumor Cell Growth In Vitro and In Vivo. PLoS ONE 8[4]: e61366 (Year: 2013).*
Raposo and Stoorvogel. 2013. Extracellular vesicles: Exosomes, microvesicles, and friends. J. Cell. Biol. 200(4):373-383 (Year: 2013).*
Vishnubhatla et al. 2014 yhe Development of Stem Cell-derived Exosomes as a Cell-free Regenerative Medicine. J. Circ. Biomark. 3:2 [doi: 10.5772/58597] (Year: 2014).*
Ainsztein et al. 2015. The NIH Extracellular RNA Communication Consortium. J. Extracell. Vesicles 4:27493 (Year: 2015).*
ExRNA-Atlas database (https://exrna-atlas.org/) Accessed Mar. 1, 2023 (Year: 2017).*
Westlab Jul. 27, 2018 Blog: What is the difference between plasma and serum? (Year: 2018).*
National Cancer Institute Apr. 23, 2018 NCI Dictionary of Cancer Terms: blood stem cell (Year: 2018).*
Murillo et al. 2019. exRNA Atlas Analysis Reveals Distinct Extracellular RNA Cargo Types and Their Carriers Present across Human Biofluids. Cell 177:463-477 (Year: 2019).*
Vader et al. 2016. Extracellular vesicles for drug delivery. Adv. Drug Deliv. Rev. 106(A):148-456 (Year: 2016).*
Afanasyeva et al. 2011. MicroRNA miR-885-5p targets CDK2 and MCM5, activates p53 and inhibits proliferation and survival. Cell Death Differentiat. 18:974-984 (Year: 2011).*
Zhang et al. 2016. miR-885-5p suppresses hepatocellular carcinoma metastasis and inhibits Wnt/B-catenin signaling pathway. Oncotarget 7[46]:75038-75051 (Year: 2016).*

Collino, Federica, et al., "Exosome and Microvesicle-Enriched Fractions Isolated from Mesenchymal Stem Cells by Gradient Separation Showed Different Molecular Signatures and Functions on Renal Tubular Epithelial Cells", Stem Cell Reviews and Reports, Humana Press Inc (2017) vol. 13, No. 2, pp. 226-243.
Anonymous, "TaqMan Advanced MiRNA Assays User Guide," Jan. 1, 2018, Retrieved from the Internet: URL: https://assets.thermofisher.com/TFS-Assets/LSG/manuals/MAN0016122_TaqManAdvmiRNAArrayCards_UG.pdf retreived on Oct. 30, 2019, pp. 1-44.
Li, Xiao, et al. "Exosome Derived From Human Umbilical Cord Mesenchymal Stem Cell Mediates MIR-181c Attenuating Burn-Induced Excessive Inflammation." EBioMedicine, vol. 8, No. C, 2016, pp. 72-82.
PCT International Preliminary Report on Patentability, International Application No. PCT/EP2019/071341, Theramir Ltd, International Filing Date Aug. 8, 2019, Mailing date Oct. 12, 2020, 39 pages.
PCT International Search Report and Written Opinion; Application No. PCT/EP2019/071341 Theramir Ltd, International filing date of Aug. 8, 2019, date of mailing Nov. 11, 2019, 13 pages.
Samstag, Yvonne, and Klemke, Martin. "Ectopic Expression of L-Plastin in Human Tumor Cells: Diagnostic and Therapeutic Implications." Advances in Enzyme Regulation, vol. 47, No. 1, 2007, pp. 118-126.
Wu, Shuai, et al. "Microvesicles Derived from Human Umbilical Cord Whartons Jelly Mesenchymal Stem Cells Attenuate Bladder Tumor Cell Growth in Vitro and in Vivo." PloS One, vol. 8, No. 4, 2013, p. e61366.
Zhang Zhuhong, Study on the mechanism of miR-885-5p in tumor growth and metastasis, Chinese Thesis, Nankai University, CN, Jan. 1, 2013, pp. 1-146, Retrieved from the internet: URL:http://cdmd.cnki.com.cn/Article/CDMD-10055-1014171696.htm Translation of p. V-p. VIII.
Zhang, Zhuhong, et al., miR-885-5p Suppresses hepatocellular carcinoma metastasis and inhibits Wnt/Beta-catenin signaling pathway. Oncotarget, vol. 7, No. 46, Nov. 15, 2016, United States ISSN: 1949-2553, DOI:10.18632/oncotarget.12602 (14 pgs).
Kilpinen et al., Expansion induced microRNA changes in bone marrow mesenchymal stromal cells reveals interplay between immune regulation and cell cycle, Aging, vol. 8(11), pp. 2799-2813 (2016).
Kilpinen et al, Supplementary material of Kilpinen et al—Expansion induced microRNA changes in bone marrow mesenchymal stromal cells reveals interplay between immune regulation and cell cycle, Aging, vol. 8(11), pp. 2799-2813 (2016).

* cited by examiner

SEQUENCE LISTING

```
<160> NUMBER OF SEQ ID NOS: 22

<210> SEQ ID NO 1
<211> LENGTH: 22
<212> TYPE: RNA
<213> ORGANISM: Homo sapiens
<220> FEATURE:
<223> OTHER INFORMATION: hsa-miR-16-5p

<400> SEQUENCE: 1
uagcagcacg uaaauauugg cg                                            22

<210> SEQ ID NO 2
<211> LENGTH: 22
<212> TYPE: RNA
<213> ORGANISM: Homo sapiens
<220> FEATURE:
<223> OTHER INFORMATION: hsa-miR-23a-5p

<400> SEQUENCE: 2
gggguuccug gggaugggau uu                                            22

<210> SEQ ID NO 3
<211> LENGTH: 22
<212> TYPE: RNA
<213> ORGANISM: Homo sapiens
<220> FEATURE:
<223> OTHER INFORMATION: hsa-miR-30a-5p
```

-continued

```
<400> SEQUENCE: 3
uguaaacauc cucgacugga ag                                              22

<210> SEQ ID NO 4
<211> LENGTH: 22
<212> TYPE: RNA
<213> ORGANISM: Homo sapiens
<220> FEATURE:
<223> OTHER INFORMATION: hsa-miR-30b-5p

<400> SEQUENCE: 4
uguaaacauc cuacacucag cu                                              22

<210> SEQ ID NO 5
<211> LENGTH: 23
<212> TYPE: RNA
<213> ORGANISM: Homo sapiens
<220> FEATURE:
<223> OTHER INFORMATION: hsa-miR-30c-5p

<400> SEQUENCE: 5
uguaaacauc cuacacucuc agc                                             23

<210> SEQ ID NO 6
<211> LENGTH: 22
<212> TYPE: RNA
<213> ORGANISM: Homo sapiens
<220> FEATURE:
<223> OTHER INFORMATION: hsa-miR-30d-5p

<400> SEQUENCE: 6
uguaaacauc cccgacugga ag                                              22

<210> SEQ ID NO 7
<211> LENGTH: 22
<212> TYPE: RNA
<213> ORGANISM: Homo sapiens
<220> FEATURE:
<223> OTHER INFORMATION: hsa-miR-30e-5p

<400> SEQUENCE: 7
uguaaacauc cuugacugga ag                                              22

<210> SEQ ID NO 8
<211> LENGTH: 22
<212> TYPE: RNA
<213> ORGANISM: Homo sapiens
<220> FEATURE:
<223> OTHER INFORMATION: hsa-miR-125b-5p

<400> SEQUENCE: 8
ucccugagac ccuaacuugu ga                                              22

<210> SEQ ID NO 9
<211> LENGTH: 23
<212> TYPE: RNA
<213> ORGANISM: Homo sapiens
<220> FEATURE:
<223> OTHER INFORMATION: hsa-miR145-5p

<400> SEQUENCE: 9
guccaguuuu cccaggaauc ccu                                             23

<210> SEQ ID NO 10
<211> LENGTH: 22
```

```
<212> TYPE: RNA
<213> ORGANISM: Homo sapiens
<220> FEATURE:
<223> OTHER INFORMATION: hsa-miR-146a-3p

<400> SEQUENCE: 10
ccucugaaau ucaguucuuc ag                                         22

<210> SEQ ID NO 11
<211> LENGTH: 22
<212> TYPE: RNA
<213> ORGANISM: Homo sapiens
<220> FEATURE:
<223> OTHER INFORMATION: hsa-miR-181c-5p

<400> SEQUENCE: 11
aacauucaac cugucgguga gu                                         22

<210> SEQ ID NO 12
<211> LENGTH: 22
<212> TYPE: RNA
<213> ORGANISM: Homo sapiens
<220> FEATURE:
<223> OTHER INFORMATION: hsa-miR-194-5p

<400> SEQUENCE: 12
uguaacagca acuccaugug ga                                         22

<210> SEQ ID NO 13
<211> LENGTH: 21
<212> TYPE: RNA
<213> ORGANISM: Homo sapiens
<220> FEATURE:
<223> OTHER INFORMATION: hsa-miR-218-5p

<400> SEQUENCE: 13
uugugcuuga ucuaaccaug u                                          21

<210> SEQ ID NO 14
<211> LENGTH: 23
<212> TYPE: RNA
<213> ORGANISM: Homo sapiens
<220> FEATURE:
<223> OTHER INFORMATION: hsa-miR-302a-3p

<400> SEQUENCE: 14
uaagugcuuc cauguuuugg uga                                        23

<210> SEQ ID NO 15
<211> LENGTH: 23
<212> TYPE: RNA
<213> ORGANISM: Homo sapiens
<220> FEATURE:
<223> OTHER INFORMATION: hsa-miR-302a-5p

<400> SEQUENCE: 15
acuuaaacgu ggauguacuu gcu                                        23

<210> SEQ ID NO 16
<211> LENGTH: 22
<212> TYPE: RNA
<213> ORGANISM: Homo sapiens
<220> FEATURE:
<223> OTHER INFORMATION: hsa-miR-335-3p

<400> SEQUENCE: 16
```

```
uuuuucauua uugcuccuga cc                                              22

<210> SEQ ID NO 17
<211> LENGTH: 23
<212> TYPE: RNA
<213> ORGANISM: Homo sapiens
<220> FEATURE:
<223> OTHER INFORMATION: hsa-miR-335-5p

<400> SEQUENCE: 17
ucaagagcaa uaacgaaaaa ugu                                             23

<210> SEQ ID NO 18
<211> LENGTH: 22
<212> TYPE: RNA
<213> ORGANISM: Homo sapiens
<220> FEATURE:
<223> OTHER INFORMATION: hsa-miR-367-3p

<400> SEQUENCE: 18
aauugcacuu uagcaauggu ga                                              22

<210> SEQ ID NO 19
<211> LENGTH: 23
<212> TYPE: RNA
<213> ORGANISM: Homo sapiens
<220> FEATURE:
<223> OTHER INFORMATION: hsa-miR-373-3p

<400> SEQUENCE: 19
gaagugcuuc gauuuugggg ugu                                             23

<210> SEQ ID NO 20
<211> LENGTH: 22
<212> TYPE: RNA
<213> ORGANISM: Homo sapiens
<220> FEATURE:
<223> OTHER INFORMATION: hsa-miR-495-3p

<400> SEQUENCE: 20
aaacaaacau ggugcacuuc uu                                              22

<210> SEQ ID NO 21
<211> LENGTH: 22
<212> TYPE: RNA
<213> ORGANISM: Homo sapiens
<220> FEATURE:
<223> OTHER INFORMATION: hsa-miR-885-5p

<400> SEQUENCE: 21
uccauuacac uacccugccu cu                                              22

<210> SEQ ID NO 22
<211> LENGTH: 22
<212> TYPE: RNA
<213> ORGANISM: Homo sapiens
<220> FEATURE:
<223> OTHER INFORMATION: hsa-let-7b-5p

<400> SEQUENCE: 22
ugagguagua gguugugugg uu                                              22
```

MICRORNA-BASED THERAPY TARGETED AGAINST LCP-1 POSITIVE CANCERS

CROSS REFERENCE TO RELATED APPLICATIONS

This application is a national phase entry under 35 U.S.C. § 371 of International Patent Application PCT/EP2019/071341, filed Aug. 8, 2019, designating the United States of America and published in English as International Patent Publication WO 2020/030750 on Feb. 13, 2020, which claims the benefit under Article 8 of the Patent Cooperation Treaty to European Patent Application Serial No. 18020374.7, filed Aug. 8, 2018, the entireties of which are hereby incorporated by reference.

FIELD OF INVENTION

The invention relates to a novel technology using miR-NAs and their ability to target and down regulate the activity of oncoproteins in LCP-1 positive cancers. The present technology designs for delivery of specific miRNA inhibitor sequences encapsulated in biological or synthetic vesicles that will affect the expression of a group of genes and proteins (including LCP1/LCP-1) associated with cancer initiation, growth, aggressiveness and metastasis.

BACKGROUND OF THE INVENTION

Cancer is a heterogeneous disease with cellular hierarchies and many different phenotypes that possess a high capacity for tumor propagation and metastasis. Progression to the metastatic stage provides the most serious challenge to effective cancer treatment and is responsible for most cancer related deaths. The invasion—metastasis cascade is a multistep cellular process that involves the spreading of cancer cells through the surrounding extracellular matrix, survival in the circulation and initial seeding, followed by subsequent expansion (colonization), in the metastatic site microenvironment. These steps necessitate a high motility for cancer cells, which is facilitated by modulation of the cellular cytoskeleton. Recent studies point to cytoskeleton binding proteins as important players in tumor metastasis, particularly due to their capacity to bind to and regulate integrin molecules. Therefore, such molecules are promising targets for inhibiting the metastatic properties of tumor cells. Specifically, some cancers express the actin reorganizing protein LCP-1 (L-Plastin, Plastin-2, lymphocyte cytosolic protein 1), which is normally leukocyte specific and not present in non-hematopoietic cells'. The protein has been recently identified as a biomarker for the early detection of various forms of cancer, such as kidney, colon, and breast cancer[2]. LCP-1 is a 70 kDa, $Ca^{2+}$-regulated and actin-binding protein that plays an important role in both the adaptive and innate immune system[3]. The plastin family of actin-binding proteins consists of three isoforms that show tissue specific expression. They exhibit a similar molecular arrangement, containing two consecutive actin binding domains in the C-terminus, each consisting of two calponin homology (CH)-domains. This structure allows LCP-1 to direct the organization of actin filaments into very tight bundles[4]. LCP-1 function is important for cells of the innate as well as the adaptive immune system. It was demonstrated that LCP-1 is crucial for immune synapse formation[5] and that it regulates integrin-dependent adhesion and migration of both granulocytes[6] and T-cells[7]. It has also been suggested that it may play a role in tumor cell motility. The actin-bundling activity of LCP-1 is known to be calcium-dependent, as increasing calcium concentrations inhibit the formation of actin-bundles. Ser5 phosphorylation was also shown to increase the actin bundling activity of LCP-1 in vitro to promote its targeting to sites of actin assembly. Regulation through phosphorylation of LCP-1 has been described as a consequence of immune responses as well as in response to signals triggering migration[8-10].

Besides the potential prognostic relevance of LCP-1 expression and phosphorylation in human cancer cells, LCP-1 represents a promising target for cancer therapy. Reduction of LCP-1 expression and/or phosphorylation in tumor cells may interfere with tumor cell aggressiveness, migration and invasion and, hence, reduce metastasis. Therapeutic tools that have been studied in order to inhibit the rate of cancer progression have been based on recombinant adenoviral vectors that are driven by the LCP1 promoter as well as on LCP-1 blocking peptides such as melittin[11]. One of the main disadvantages of adenoviral vectors is that cell-specific targeting is difficult to achieve as the virus has no envelope to attach cell-specific ligands to, while there are also important safety concerns such as the potential generation of replication competent virus and the possibility of provoking an inflammatory response in the patient, particularly when repeated administrations are given. In addition, LCP-1 blocking peptides such as melittin have strong hemolytic properties that make them toxic to normal cells and thus, non-suitable for direct clinical applications[15]. Therefore, the purpose of our invention is the development of a novel technology for the successful and targeted inhibition of LCP-1. Simultaneously, a group of associated proteins (Protein Panel, Table 1) represent additional novel targets for cancer therapy and are thus utilized in our invention together with LCP-1 in order to develop customized targeted cancer therapeutics.

TABLE 1

Selected PANEL of associated proteins, genes & miRNAs
Selected PANEL of associated proteins, genes & miRNAs

| | |
|---|---|
| Proteins | Protein argonaute-2, Proto-oncogene c-Akt, Annexin A3, Amyloid-beta A4 protein, Apoptosis regulator Bcl-2, Bcl-2-associated transcription factor 1, Bcl-2-like protein 2, Baculoviral IAP repeat-containing protein 5, Bone morphogenetic protein 1, cancer susceptibility candidate 7, G1/S-specific cyclin-D1, CD44 antigen, Cadherin-2, Cadherin-11, Cyclin-dependent kinase 2, Cyclin-dependent kinase inhibitor p27, CCAAT/enhancer-binding protein alpha, Cytochrome c oxidase subunit 2, Catenin beta-1, C-X-C chemokine receptor type 4, Dickkopf-related protein 1, Epidermal growth factor receptor, Fatty acid synthase, High mobility group protein HMGI-C, Insulin-like growth factor 1 receptor, Insulin-like growth factor 2 mRNA-binding protein 2, Transcription factor AP-1, Mitogen-activated protein kinase kinase kinase kinase 4, Induced myeloid leukemia cell differentiation protein Mcl-1, DNA replication licensing factor MCM5, E3 ubiquitin-protein ligase Mdm2, 72 kDa type IV collagenase, Matrix metalloproteinase-9, Metastasis- |

TABLE 1-continued

Selected PANEL of associated proteins, genes & miRNAs
Selected PANEL of associated proteins, genes & miRNAs

|  |  |
|---|---|
|  | associated protein MTA3, Mucin-13, Nuclear factor NF-kappa-B p105 subunit, Phosphatidylinositol 4,5-bisphosphate 3-kinase catalytic subunit alpha isoform, Urokinase plasminogen activator surface receptor, Tumor necrosis factor ligand superfamily member 11, Ras GTPase-activating protein 1, Roundabout homolog 1, Slit homolog 2 protein, Zinc finger protein SNAI2, Mothers against decapentaplegic homolog 3, Zinc finger protein SNAI1, Transcription factor SOX-2-OT, Transcription factor Sp1, TGF-beta receptor type-2, Transforming growth factor beta-1, Vascular endothelial growth factor A, Proto-oncogene Wnt-1 |
| Genes | AGO2, AKT1, ANXA3, APP, BCL2, BCLAF1, BCLW, BIRC5, BMP1, CASC7, CCND1, CD44, CDH2, CDH11, CDK2, CDKN1B, CEBPA, COX2, CTNNB1, CXCR4, DKK1, EGFR, FASN, HMGA2, IGF1R, IGF2BP2, JUN, LCP1, MAP4K4, MCL1, MCM5, MDM2, MMP2, MMP9, MTA3, MUC13, NFKB1, PI3KCA, PLAUR, RAB23, RANKL, RASA1, ROBO1, SLIT2, SLUG, SMAD3, SNAIL, SOX2OT, SP1, TGFBR2, TGFB1, VEGFA, WNT1 |
| miRNAs | miR-16-5p, miR-23a-5p, miR-125b-5p, miR-145-5p, miR-146a-3p, miR-181c-5p, miR-218-5p, miR-495-3p, let-7b-5p, miR-30a-5p, miR-30b-5p, miR-30c-5p, miR-30d-5p, miR-30e-5p, miR-194-5p, miR-302a-3p, miR-302a-5p, miR-335-3p, miR-335-5p, miR-367-3p, miR-373-3p, miR-885-5p |

RNA-based approaches are considered the next major class of cancer therapeutics. Advancements in genetics relating to the role of RNA in an ever-expanding range of cellular pathways and processes have shown that RNA has many of the genetic and regulatory properties formerly attributed only to DNA and proteins. Current work is focused mainly on modified-mRNA to promote expression of therapeutic proteins and on RNAi variants (such as siRNA and miRNA), which can either silence or amplify genes in cancer cells.

MiRNAs, a class of small (~22 nucleotides long), non-coding RNA that bind to messenger RNAs (mRNAs), acting as endogenous post-translational gene regulators[12]. The interaction between miRNAs and mRNAs is highly complex and currently not completely understood. However, approximately one-third of human protein-encoding genes are regulated by miRNAs, underlining their extraordinary impact on protein expression. What is known is that, at least in mammals, miRNAs bind through imperfect complementarity to their target genes[13]. Several mechanisms of action have been proposed for miRNA-mediated gene repression. Protein synthesis may be suppressed by inhibition of translational initiation, mRNA degradation due to deadenylation or, in rare cases, mRNA cleavage. Re-expressing lost miRNAs in a cell can deliver a dramatic effect, because miRNAs regulate a vast number of genes and pathways. Both miRNA re-expression and downregulation have been shown to have anti-tumor effects while re-expressing a tumor suppressor miRNA can downregulate multiple oncogenes. Re-expression, to physiological levels, of tissue-specific miRNAs that are down-regulated in cancer can induce the de-differentiation of cancer cells.

The success of RNA therapeutics hinges on their effective and safe delivery to their molecular targets inside cancer cells, as the early failures in clinical trials have demonstrated. Thus, new, innovative drug delivery technologies are necessary in order to fully realize their full potential in cancer therapy. The systemic delivery of miRNAs faces its own set of limitations. The size of unconjugated RNA is 7-20 kDa, and it is well known that molecules with a size less than 50 kDa are filtered by the kidneys and removed from circulation (excreted). Unlike many other drugs, miRNAs do not freely diffuse into cells and, since they tend to be unstable, can potentially get degraded once they enter a cell. Thus, effective therapeutic strategies need to ensure the efficient delivery to tumor sites and, equally crucial, the successful insertion of functional sequences into the target cells. In addition, a major obstacle to systemic delivery is that oligonucleotide-based therapies may induce adverse effects such as aggregation, liver toxicity and stimulation of the immune response by increasing IFN production in patients.

Current approaches to the delivery of miRNAs in vivo include anti-miRNA oligonucleotides, antagomiRs, locked nucleic acid (LNA), miRNA sponges, vector-based systems, liposomes and nanoparticles. Each approach comes with advantages but also significant disadvantages; for particle-based approaches major limitations include the inefficient endocytosis by target cells and the ineffective endosomal release. Reintroducing a miRNA using a viral system carries its own set of possible hazards, as there is always a risk of insertional mutagenesis, activation of oncogenes and a strong immunological response. For liposomal delivery systems, the inefficiency of targeting tumors and delivering their therapeutic payload in vivo has led to significant complications and side effects as demonstrated in the early clinical trials of the first miRNA-based therapeutics.

BRIEF DESCRIPTION OF DRAWINGS

The patent or application file contains at least one drawing executed in color. Copies of this patent or patent application publication with color drawing(s) will be provided by the Office upon request and payment of the necessary fee.

Figure 5:
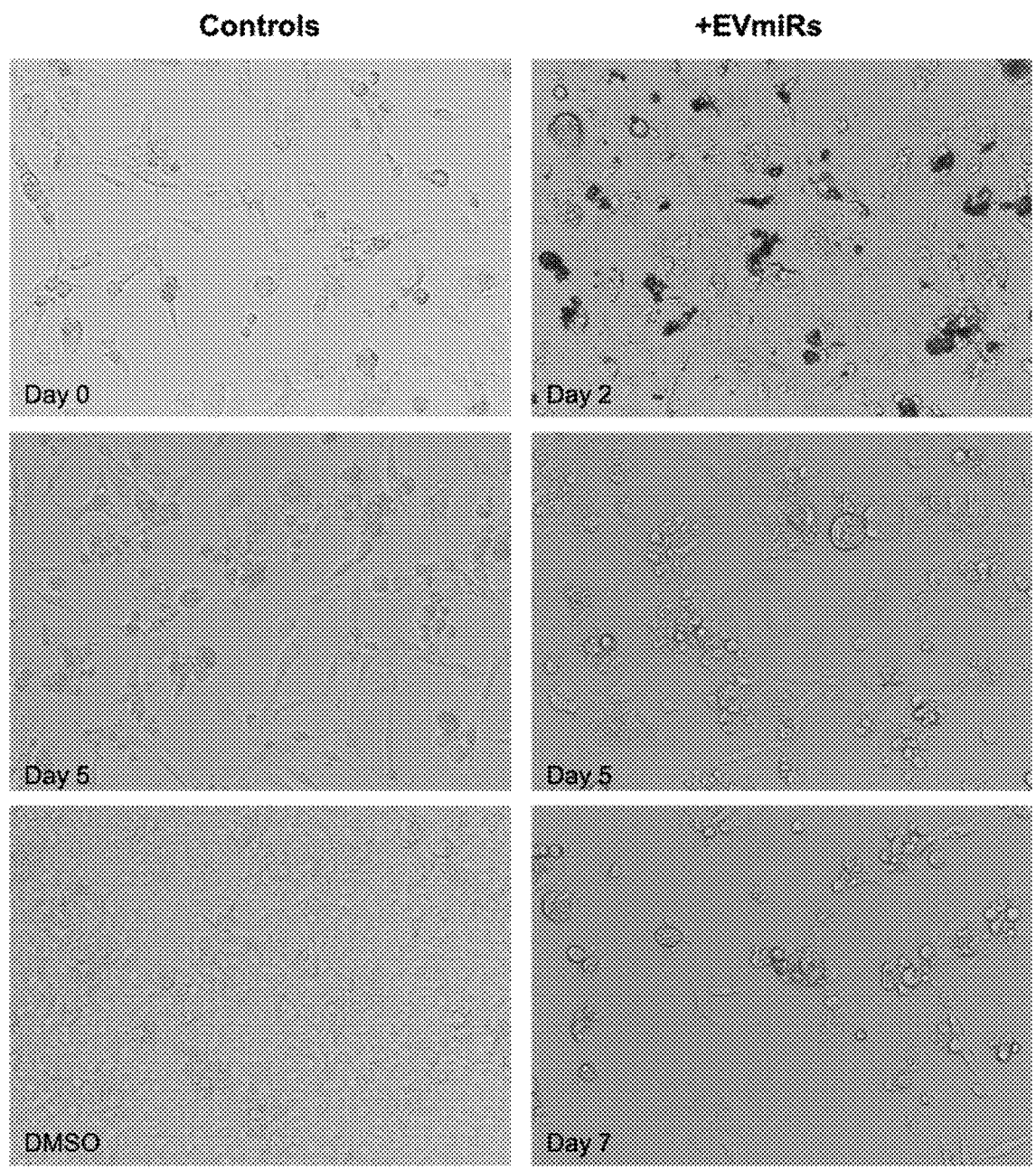

FIG. 5. In vitro experiments of MDA-MB-231 cells in treatment with EVmiRs confirmed their internalization and the induction of a biological effect as evidenced by membrane damage, cell shrinkage and blebbing in the targeted cells (at various time points such as Day 2, 5 and 7 of the treatment). Control cells with no treatment or with DMSO treatment are shown for comparison.

Figure 6A:
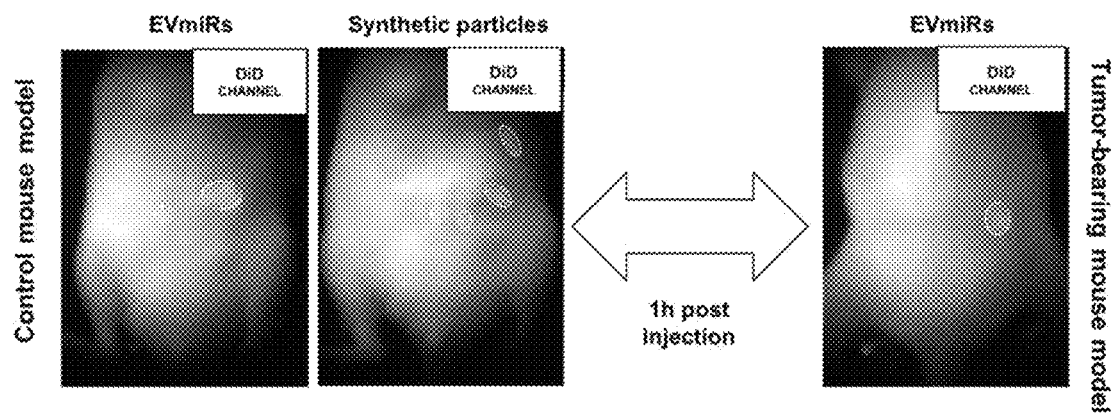
Figure 6B:
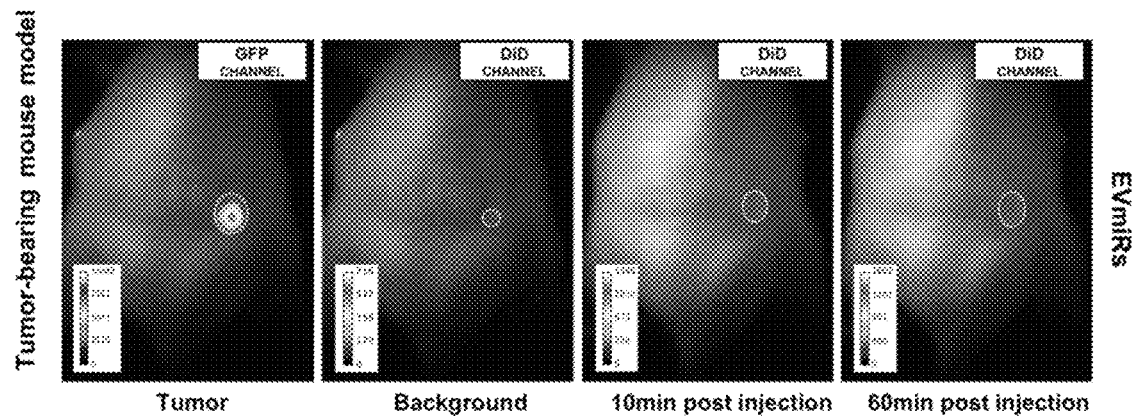

FIG. 6. In vivo whole-body biodistribution assay. FIG. 6A Labeled EVmiRs (DiD stained) and synthetic DiD-stained particles were administered to control mice. Labeled EVmiRs (DiD stained) were administered in tumor-bearing mice that were tumor-GFP-labeled. FIG. 6A shows co-localization of EVmiRs with the tumor site. Fluorescence has been surrounded by dashed lines. FIG. 6B. Animals were tested at different time-points for in vivo biodistribution using an in-house developed fluorescence imaging system. Co-localization of EVmiRs (fluorescence has been surrounded by dashed lines) with the tumor site (tumor has been surrounded by dashed lines in the left-handed panel) was evident for different time points.

Figure 7:
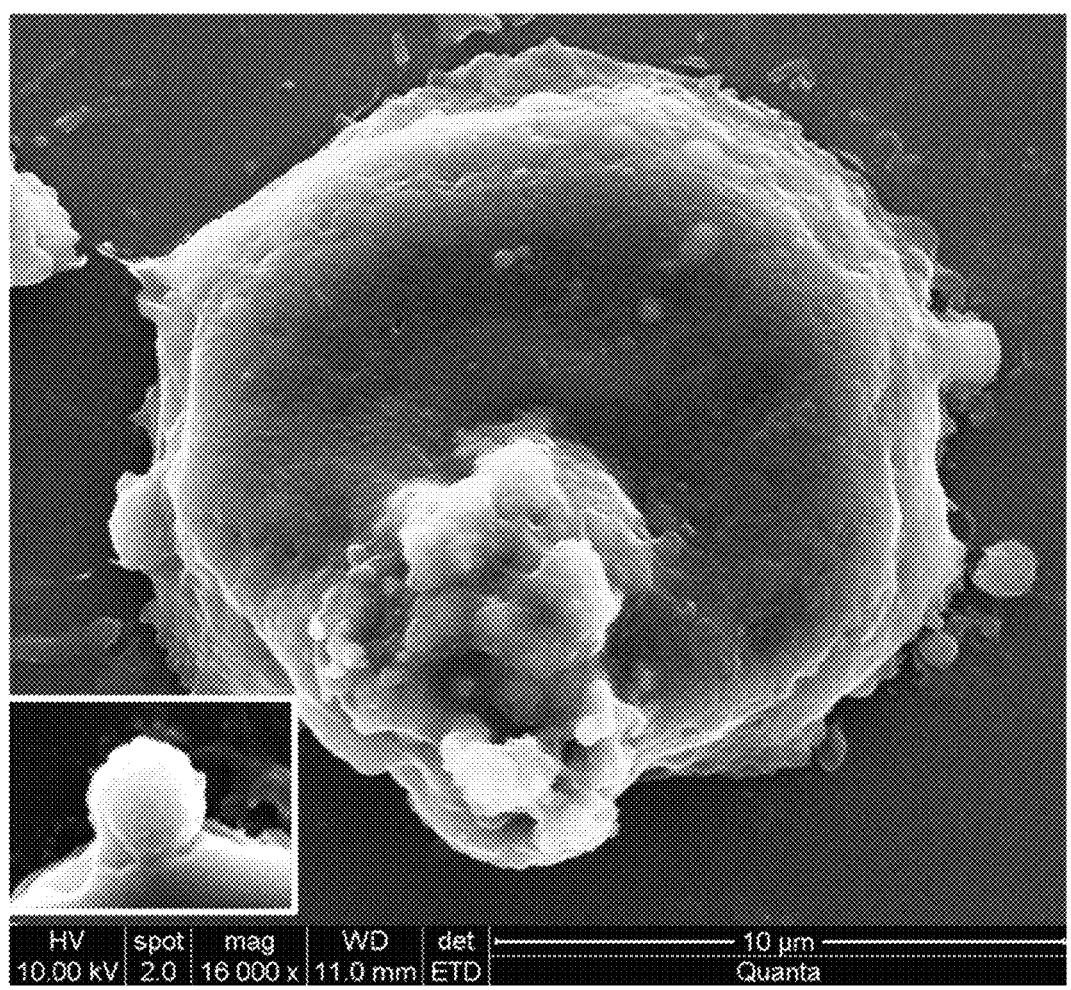

FIG. 7. Small image shows scanning electron micrograph of EVmiR and larger image shows the attack of EVmiRs against the MDA-MB-231 breast cancer cell line. EVmiRs co-localize with the tumor cells and load their contents though membrane uptake mechanisms.

SUMMARY OF INVENTION

Figure 1:
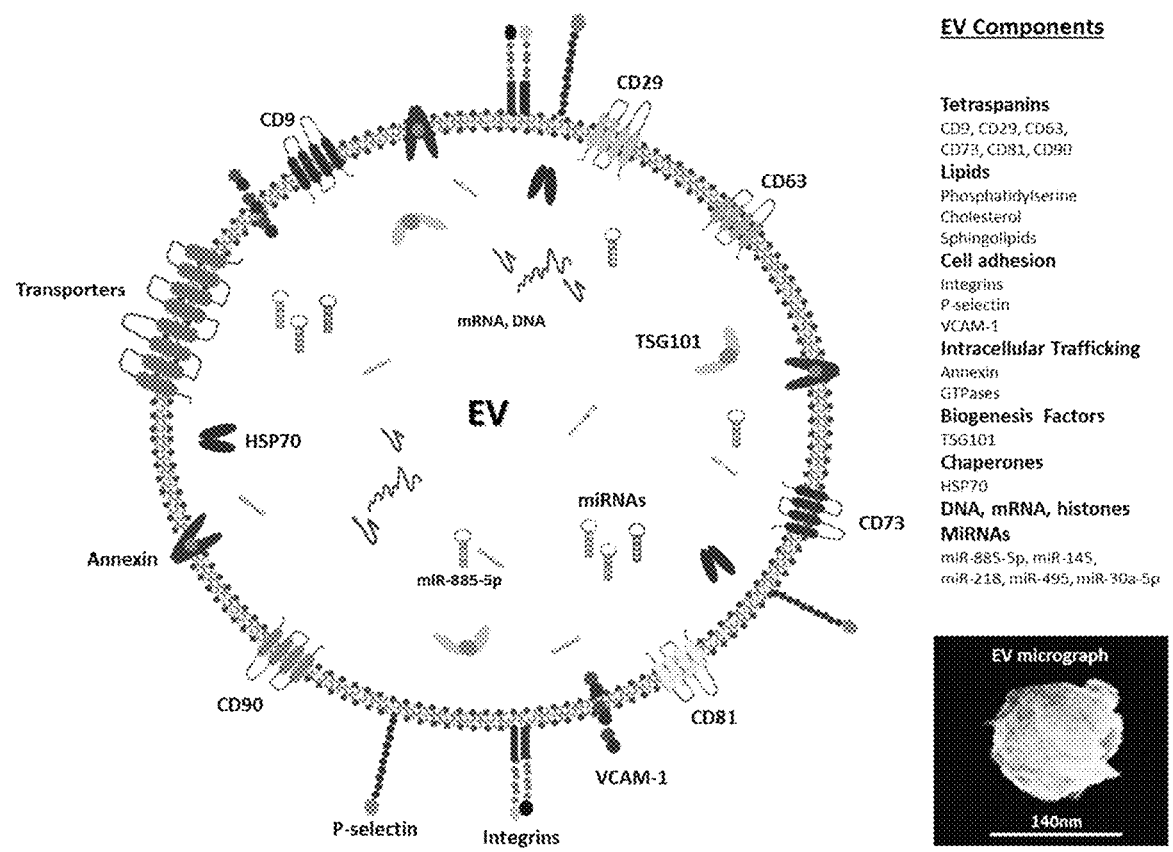
FIG. 1. Graphic representation of the EVmiR™ construct. The EVmiR™ is composed by a lipid bilayer of cell membrane origin, membrane proteins, CDs, transporters and others. They contain naturally occurred miRNAs as well as patient-specific miRNAs such as miR-885-5p that directly targets the expression of LCP-1 protein. Also shown here a micrograph of the EVmiR™ analyzed using scanning electron microscopy (SEM) with a size of 140 nm.

The present invention designs for delivery of a specific combination of miRNA sequences (including miR-885-5p) encapsulated in carriers of biological or synthetic origin (size 30-300 nm) containing chemotactic factors and proteins of stem cell origin (Table 2). The proposed construct titled EVmiR™ (FIG. 1) will affect the action of a group of genes and proteins (including LCP1/LCP-1) associated with cancer initiation, growth, aggressiveness and metastasis in LCP-1 positive cancers (Table 1).

TABLE 2

The main components of the engineered EVmiR ™ construct.
Carrier Components

| | |
|---|---|
| Proteins | P-selectin, Integrin beta-1, Vascular cell adhesion protein 1, Annexins, Tumor susceptibility gene 101 protein, Hsp70-binding protein 1, etc. |
| Cluster of Differentiation+ | CD9, CD29, CD63, CD73, CD81, CD90, etc. |
| Cluster of Differentiation− | CD31, CD34, CD45, etc. |
| Endogenous miRNAs | miR-16-5p, miR-23a-5p, miR-125b-5p, miR-145-5p, miR-146a-3p, miR-181c-5p, miR-218-5p, miR-495-3p, let-7b-5p, etc. |
| Additional miRNAs (synthetic or de novo-induced) | miR-30a-5p, miR-30b-5p, miR-30c-5p, miR-30d-5p, miR-30e-5p, miR-194-5p, miR-302a-3p, miR-302a-5p, miR-335-3p, miR-335-5p, miR-367-3p, miR-373-3p, miR-885-5p, etc. |

A therapeutic system based on specific miRNAs selected from a panel that includes the sequence miR-885-5p, and are loaded within biological, synthetic or chemical formulations including extracellular vesicles. This construct targets and modulates the expression of a specific group of oncoproteins (including LCP-1) that are associated with cancer initiation, growth, aggressiveness and metastatic potential in LCP-1 positive cancers. The successful delivery system is of a narrow size range (30-300 nm diameter) with stem cell associated properties of biological or synthetic origin. These vesicles act as targeted carriers of specific therapeutic miRNA sequences and once administered, migrate to tumor sites in order to fuse with, and deliver their therapeutic load directly into cancer cells.

PROBLEM: Cancer drugs currently in the market have yet to achieve the thorough eradication of tumors and the effective remedy of cancer disease in human patients. This is mainly due to difficulties in blocking the complex cancer growth and metastasis process (therapeutic efficiency) as well as due to inadequate delivery of therapeutic agents to tumor sites (tumor targeting). This lack of effective therapeutic options opens the door to new opportunities for novel approaches for targeted delivery of cancer therapy that can intervene in multiple cancer cell processes. Development of metastasis causes the most serious clinical consequences of cancer and is responsible for over 90% of cancer related deaths'. The process of cancer growth and metastasis is complex and our understanding of the molecular mechanisms that regulate them remain limited. The discovery of key targets in the oncology field will open new avenues for the fight against a broad range of cancer types such as melanoma, glioblastoma, ovarian, breast, cervical, colorectal and prostate cancer etc. Tumor cell migration and metastasis require dynamic rearrangements of the actin cytoskeleton. Interestingly, LCP-1 is responsible for the organization of actin filaments and is also aberrantly expressed in the many types of blood cells. We have identified that the increased expression of this protein in epithelial cancers activates the metastasis pathway through the circulatory system allowing metastasis in distant sites in combination with other signature genes (Genes Panel, Table 1). Similarly, the identification of an ever-expanding list of oncoproteins that play a role, not only in metastasis, but also in initiation and growth of primary tumors linked to LCP-1 will open up a wealth of opportunities in the oncology field to design and develop novel cancer therapeutics that can target multiple stages of the disease.

SOLUTION: Tumor cell initiation, migration and metastasis require dynamic rearrangements of the cell cytoskeleton and the activation of key oncogenic pathways. Interestingly LCP-1 protein, originally described as a leukocyte specific protein, is aberrantly expressed in several malignant tumors and interacts with several other cancer-associated proteins such as the ones described in Table 1 (Protein Panel). Therefore, we have developed a panel of associated miRNAs (miRNA Panel, Table 1), and we have utilized it to design custom combinations of therapeutic miRNAs that can interfere with the expression of the above cancer associated proteins via targeting of their respective genes (see Genes Panel, Table 1).

In our invention, the therapeutic miRNAs are administered to tumors via a novel delivery system based on extracellular vesicles (EVs), although our panel of miRNAs can also be delivered with any other tumor-targeting carrier system (such as nanoparticle- or liposome-based systems). Thus, administration of our custom miRNA combinations described herein may be accomplished by any acceptable method that allows the miRNA or nucleic acid encoding the miRNA to reach its target. In a particular embodiment of the invention, EVs have been specifically engineered to deliver our therapeutic miRNAs to tumor sites and inside cancer cells. The EVmiR™ complexes are engineered extracellular vesicles (EVs) of stem cell origin containing specific miRNA sequences that act as direct inhibitors of LCP-1. The EVmiR™ is also engineered to target and manipulate the expression of another group of oncoproteins that is directly involved in the LCP-1 pathway and mainly upregulated in solid tumors (Protein Panel, Table 1). The EVmiR™ complexes are ideal delivery vehicles as they retain the membrane receptors that allow stem cells to home selectively into tumor sites and target malignant cells, thus avoiding the targeting of healthy cells. The EVs home and engraft in solid tumors via specific chemokine receptors, fuse to tumor cell membranes, and incorporate miRNA directly into the target cancer cell, thus exerting their therapeutic effect while minimizing side effects associated with conventional therapies. These EVmiR™ complexes offer enhanced prophylactic and therapeutic potential due to their ability to target multiple molecules in malignant cells when compared with approaches targeting single genes and induce immunosuppression through cytokine signaling inhibition making this approach especially suitable as component of therapeutic strategies in recurring cancer disease.

In our invention, we target, both in vitro and in vivo, the cancer related protein LCP-1 (as well as the oncoproteins in Table 1) via delivery of a combination of miRNAs encapsulated within the EVmiR™ or other appropriate vesicles.

We have constructed a novel cellular EVmiR™ complex containing a group of naturally occurring and synthetically overexpressed miRNAs (either by using synthetic premiRs, mature miRs, antimiRs or actively de novo induced miRs). The EVs are intact vesicles, with a size of 30-300 nm in diameter, formed from the plasma membrane and enriched in cytoplasmic components, cell surface proteins and bioactive phospholipids derived from the plasma membrane of their parent cells (see Table 2). This customized complex directly targets the expression of LCP-1 and other cancer related proteins (Table 1) that are specifically found in the tumor environment and which can block cancer processes such as tumor growth and metastatic progression. We have found that miRNAs associated with cellular particles such as our engineered EVs are protected from nuclease degradation and are able to be transferred in a variety of cells in order to prophylactically or therapeutically alter the gene expression of the recipient cells.

In certain embodiments, the panel may comprise naturally occurring miRNAs of stem cell origin and (one or more) synthetically overexpressed miRNAs, wherein the synthetically overexpressed miRNAs are synthetic premiRs, mature miRs, antimiRs or de novo induced miRs.

Our invention is applied prophylactically and therapeutically as part of a broader personalized medical strategy that includes appropriate patient selection as well as diagnostic, prognostic, therapeutic and monitoring components. The benefits of our invention, an improved pharmaceutical offering that has high selectivity and lower toxicity than earlier options, will be multifactorial. The cost of treating non-tolerated toxicities will be reduced and time of completion of active treatment will be significantly decreased due to the fact that toxic effects will not have to interrupt treatments. Optimized patient selection will be based on molecular profiling of the tumor and patient response variables paving the way for more efficient drug use and leading to lower mortality and morbidity rates. For this purpose, a companion diagnostic kit for assaying the levels of LCP-1 and the other oncoprotein targets, as well as monitoring the expression of our panel of miRNAs in tissue and/or liquid biopsies, has been developed. Thus, the EVmiR™ approach for targeted cancer therapy has been validated by utilizing the kit on clinical samples of tumors expressing the targeted oncoproteins and associated miRNA sequences.

ADVANTAGES: In the last 20 years, the oncology field has witnessed the introduction of a new class of drugs based on the concept of targeted therapy—drug treatments developed to selectively target genes, proteins and signaling pathways that have been shown to play a role in cancer development. Several targeted therapies have shown efficacy in a wide range of cancers and more are being continuously introduced, driven by new knowledge in molecular biology and advances in chemical and molecular synthesis as well as in high-throughput screening methods (the "omics" revolution). Among the new crop of therapeutic agents in the market or under development, angiogenesis inhibitors, immunotherapeutic agents (monoclonal antibodies, cytokines and cancer vaccines), kinase signaling inhibitors and gene (DNA or RNA based) therapy seem to be the most promising. RNA (mRNA and RNAi) based approaches have been attracting considerable interest the last few years, as aberrant RNA regulation has been increasingly implicated in a range of cellular pathways and processes critical to cancer development.

Therefore, the market for targeted RNA-based therapies is still in its infancy and at the very early stages of development. The recent breakthroughs in elucidating the crucial role for RNA in a host of cellular mechanisms have facilitated the emergence of novel approaches for engineering mRNA and RNAi sequences into clinically approved therapeutics. These technologies aim to take advantage of the body's own natural processes, to either promote expression of beneficial proteins or silence genes and eliminate specific proteins in cancer cells, leading to the development of safer cancer therapeutics with vastly improved specificity and efficacy. Depending on the type and location of the targeted cancer, the delivery of the therapeutic agents often requires the development of novel transport technologies such as nanocapsules, nanoparticles, liposomes and PEG-ylated vesicles in order to minimize toxicity to healthy tissues and maximize effective therapeutic concentrations at the tumor site.

Our invention will offer significant advantages as targeted RNA-based therapy for cancer:
- Targeted delivery remains a major challenge for RNA therapeutics. Our in vivo studies have shown that mesenchymal stem cells can selectively migrate to tumors (homing), thus, the EVmiR™ complexes incorporate the necessary membrane receptors that will allow for the targeted delivery of miRNA to the tumor site. The unique specificity of the approach translates into increased efficacy against tumors, by avoiding the targeting of healthy cells and minimizing potential side effects.
- A key obstacle to effective miRNA-based therapy is the requirement for stability and successful delivery into target tissues. Unlike many other drugs, miRNAs do not freely diffuse into cells; thus, miRNAs require special delivery approaches to achieve the desired effect. We have demonstrated that the EVmiR™ complexes can fuse with the target cancer cells and allow therapeutic miRNA to incorporate into recipient cells.
- EVs can deliver therapeutic doses of miRNAs that have been shown to affect multiple pathways that are involved in cancer development. Specific miRNAs have already been identified, which regulate gene expression in cancer cells both through reduction or deletion of oncogenic miRNA and through amplification or overexpression of tumor suppressing miRNA.

Thus, compared to earlier approaches targeting single genes, the miRNA approach may present opportunities to target multiple molecules in cancer cells, and thus offer multiple avenues for tumor reduction with a single approach.

Unlike earlier RNA therapies, the EVmiR™ complexes do not elicit an innate immune response since the therapeutic miRNA sequences are not exposed. Instead, these EVs have been shown to induce immunosuppression (through cytokine inhibition), which renders the targeted delivery approach more effective, especially in recurring cases.

This invention represents a new clinical cancer therapeutic modality, with potential for significant commercialization and applications in future clinical investigations into the treatment of malignancies. This invention will lead to the rapid development of marketable products and services for patients and the transformation of the cancer treatment field by creating new knowledge on the pathology of tumors and allowing for the customization and personalization of treatments.

DETAILED DESCRIPTION

Collectively, 22 miRNAs are used in this embodiment in order to reduce tumor growth and metastasis in LCP-1 positive cancers. Stem cell-derived miRNAs (9 miRs naturally occurring) are assigned to be always present in the therapeutic cocktail responsible for targeting of cancer cells and reduction of the growth, invasion and proliferation of tumors. On the other hand, 13 miRNAs (synthetically or de novo induced) may be used either selectively or in total depending on the diagnostic profile of selected patients. The miRNA cocktail will be mainly administered by means of the EVmiR™ complex but not limited to this formulation. Examples for the production and use of the technology are given below:

EV production: The present embodiment provides a method of treating cancers that are positive for LCP-1, as well as for any of the other oncoproteins from Table 1 (Protein Panel), with the EVmiR™ complex containing:
a) specific miRNAs that are able to downregulate the targeted oncoproteins (given in Table 1)
b) specific cell membrane proteins that enable EVs to target and home to sites of tumor growth and metastasis (given in Table 2)

The EVs (size range 30 to 300 nm) are produced from stem cells or progenitor cells that are sourced from the umbilical cord, cord blood, Wharton's jelly, blood, or bone marrow (stem cells may be also of mesenchymal origin). The stem cell cultures are subject to stress conditions, leading to the formation of EVs (secreted membrane vehicles <300 nm in diameter, including exosomes and microvesicles) which are harvested, purified and concentrated. EVs are enriched in cytoplasmic components, cell surface proteins and bioactive phospholipids that are derived from the plasma membrane of their parent cells, such as P-selectin, Integrin beta-1, Vascular cell adhesion protein 1 Annexins, Tumor susceptibility gene 101 protein and Hsp70-binding protein 1, and are characterized as $CD9^+$, $CD29^+$, $CD63^+$, $CD73^+$, $CD81^+$, $CD90^+$, $CD31^-$, $CD34^-$ and $CD45^-$. Stem cell/progenitor cell/mesenchymal stem cell-derived EVs are also enriched with endogenous miRNAs such as miR-16-5p, miR-23a-5p, miR-125b-5p, miR-145-5p, miR-146a-3p, miR-181c-5p, miR-218-5p, miR-495-3p, let-7b-5p (Table 3) and can be custom designed/produced with additional miRNAs that are normally under-expressed or not present in the parent cells (Table 4). We have utilized these EVs to construct a novel cellular EV-miRNA complex (EVmiR™) that carries a range of miR-NAs including the overexpressed miR-885-5p sequence. This complex can be customized to directly target the cancer related protein LCP-1, which is specifically expressed in the tumor environment, and block LCP-1 dependent cancer processes such as tumor growth and metastatic progression. Similarly, the EVmiR™ based approach can be further customized to target additional oncoproteins (see Table 1), thus ensuring that our invention can target and treat as wide a range of cancer types as possible.

Optimizing EVs by loading specific miRNAs: EVs loaded with specific miRNAs (e.g. miR-885-5p and others selected from Table 1) are produced following the induced overexpression of the target sequences.

Genetically perturbing the expression of individual miR-NAs or their targeted transcripts promotes bidirectional miRNA relocation from the cell cytoplasm to P-bodies and controls miRNA sorting to EVs. We have employed several methods to achieve the effective loading of stem cell derived EVs with the desired miRNA sequences, which are described below (here using, but not limited to, miR-885-5p as an example).

Similarly, our proprietary EVmiR™ complexes can be loaded with specific antagomiRs in order to inhibit/block miRNAs that are upregulated in specific cancer types, in the context of a therapeutic miRNA inhibition strategy. The specific antagomiRs can be loaded as inhibitory sequences ("antagonists") of the target sequences of interest and can be delivered via EVs in order to inhibit oncogenic miRNAs in specific cancers.

Figure 2:
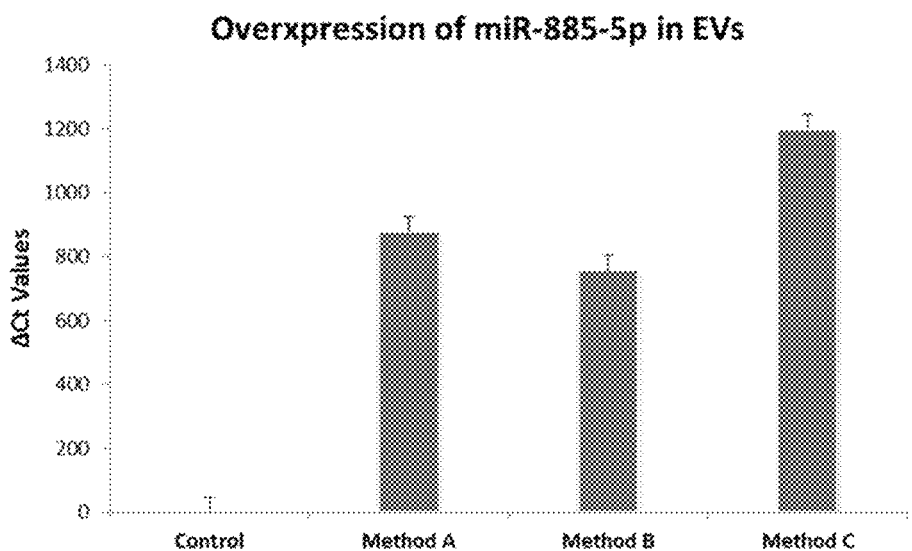
FIG. 2. Validation of the miRNA loading methods of EVmiR™ construct. Assessing the expression levels of miR-885-5p (by using real-time PCR) in EVs using three different overexpression approaches (Methods A, B and C).

Method A. (Pre-loading approach). Overexpression of miR-885-5p may be carried out by induced overexpression in the parent cell with the use of: i) Transfection of the parent stem cells with pre-miR-885-5p or synthetic miR-885-5p that mimics the endogenous, mature miR-885-5p; ii) Sumoylated hnRNPA2B1 that can direct the loading of miR-885-5p into EVs; iii) Re-engineered exo-motif-containing miR-885-5p (FIG. 2). This method can be applied to the pre-loading of EVs using other specific miRNA sequences selected from Table 4.

Method B. (Post-loading approach). Loading miRNAs directly in the EVs following generation from the parent cells. Another method used for producing EVs loaded with specific miRNAs (such as, but not limited to, miR-885-5p) is by direct transfer of synthetic miR-885-5p and other specific miRNAs (selected from Table 4) in the EVs via chemical insertion and/or electroporation and/or sonoporation (FIG. 2).

Method C. (De novo induction). We have also determined that the chemokine ligand CXCL7 is responsible for the de novo induction of miR-885-5p when applied to the parent cells. This can be used as an alternate method for inducing expression of the native miR-885-5p in the stem cell-derived EVs (FIG. 2).

Method D. (Emptying/reloading EVs). Emptying EVs of their endogenous miRNAs (via sonication, saponin permeabilization etc.) and reloading via incubation of the emptied EVs with specific miRNAs is another method that can be utilized to produce customized EVmiR™ complexes (FIG. 2).

As an example, in our invention we showed that LCP1, CDK2, MCM5, WNT/CTNNB1, CASC7/AGO2 are definite targets of miR-885-5p in vitro, in a range of cancer cell lines tested (CaCo2, RKO, HT-29, MDA-MB-231, MCF-7, SKOV3, EFO-21, LNCaP and THP-1) and in vivo, in orthotopic mouse models of breast and colon cancer. We have further developed a novel system for miRNA delivery applicable for both local and systemic administration with the use of stem cell-derived EVs. Our invention indicates that LCP-1 protein is a definite target of miR-885-5p. In vitro comparative-omics studies have demonstrated that changes in miR-885-5p expression can modulate protein levels in LCP-1 positive cells. To establish a mechanistic link, expression levels of miR-885-5p were altered by transfecting a range of cancer cell lines with miR-885-5p inhibitors and precursors. The inhibitor sequence, anti-miR-885-5p, is a chemically modified, single stranded nucleic acid designed to specifically bind to and inhibit the endogenous miRNA. Pre-miR-885-5p mimics the endogenous, mature miR-885-5p. The overexpression (using pre-miR) and the inhibition (using anti-miR) of miR-885-5p were validated by real-time qPCR and quantitative Western blots. The data demonstrates that overexpression of miR-885-5p leads to knock-down of endogenous LCP-1, while transfection of cancer cells with the precursor miRNA for miR-885-5p leads to a compromised ability for migration and metastasis; thus, miR-885-5p upregulation inhibits LCP-1 expression and alters cell function by inhibiting tumor cell growth and metastatic potential.

The present invention provides the panel of miRNAs as taught herein, or the EVs as taught herein, for use in (a method of) treating LCP-1 positive cancer in a patient.

Except when noted, "subject" or "patient" are used interchangeably and refer to animals, preferably warm-blooded animals, more preferably vertebrates, even more preferably mammals, still more preferably primates, and specifically includes human patients and non-human mammals and primates. Preferred subjects are human subjects.

The term "mammal" includes any animal classified as such, including, but not limited to, humans, domestic and farm animals, zoo animals, sport animals, pet animals, companion animals and experimental animals, such as, for example, mice, rats, hamsters, rabbits, dogs, cats, guinea pigs, cattle, cows, sheep, horses, pigs and primates, e.g., monkeys and apes. Particularly preferred are human subjects, including both genders and all age categories thereof.

A related aspect provides a method of treating LCP-1 positive cancer in a patient in need of such a treatment, comprising administering a therapeutically effective amount of a panel of miRNAs as taught herein or EVs as taught herein to the patient.

A related aspect provides the use of a panel of miRNAs as taught herein or EVs as taught herein for the manufacture of a medicament for the treatment of LCP-1 positive cancer in a patient.

As used herein, a phrase such as "a subject in need of treatment" includes subjects that would benefit from treatment of a given condition, particularly LCP-1 positive cancer. Such subjects may include, without limitation, those that have been diagnosed with said condition, those prone to develop said condition and/or those in who said condition is to be prevented.

The terms "treat" or "treatment" encompass both the therapeutic treatment of an already developed disease or condition, such as the therapy of an already developed LCP-1 positive cancer, as well as prophylactic or preventive measures, wherein the aim is to prevent or lessen the chances of incidence of an undesired affliction, such as to prevent occurrence, development and progression of LCP-1 positive cancer. Beneficial or desired clinical results may include, without limitation, alleviation of one or more symptoms or one or more biological markers, diminishment of extent of disease, stabilised (i.e., not worsening) state of disease, delay or slowing of disease progression, amelioration or palliation of the disease state, and the like. "Treatment" can also mean prolonging survival as compared to expected survival if not receiving treatment.

The term "prophylactically effective amount" refers to an amount of an active compound or pharmaceutical agent that inhibits or delays in a subject the onset of a disorder as being sought by a researcher, veterinarian, medical doctor or other clinician. The term "therapeutically effective amount" as used herein, refers to an amount of active compound or pharmaceutical agent that elicits the biological or medicinal response in a subject that is being sought by a researcher, veterinarian, medical doctor or other clinician, which may include inter alia alleviation of the symptoms of the disease or condition being treated. Methods are known in the art for determining therapeutically and prophylactically effective doses for the EVs as taught herein.

In parallel, we have developed a companion diagnostic kit to enable the customized formulation of exogenous miRNA sequences in our EVmiR™ complexes depending on the specific cancer targeted. The proprietary panel can measure/ quantify miRNA levels in liquid (blood, urine, exosomes etc.) and tissue biopsies as well as assess expression levels of a set of at least five oncoproteins, for instance of a set of five oncoproteins (selected from Table 1 and including LCP-1) that are known to be upregulated in the specific cancer type targeted. The companion diagnostic kit allows analysis of miRNA profiling of the patients' samples based on a panel of endogenous and/or exogenous miRNAs. If miRNAs are found to be downregulated, these miRNAs can be included in the EVs, e.g. EVmiR approach.

Hence, an aspect relates to a kit of parts comprising means for determining the level of expression of a panel of miRNAs comprising miR-30a-5p, miR-30b-5p, miR-30c-5p, miR-30d-5p, miR-30e-5p, miR-194-5p, miR-302a-3p, miR-302a-5p, miR-335-3p, miR-335-5p, miR-367-3p, miR-373-3p, and miR-885-5p, in a sample from a patient, preferably a human subject. In certain embodiments, the kit comprises primers capable of specifically binding miR-30a-5p, miR-30b-5p, miR-30c-5p, miR-30d-5p, miR-30e-5p, miR-194-5p, miR-302a-3p, miR-302a-5p, miR-335-3p, miR-335-5p, miR-367-3p, miR-373-3p, and miR-885-5p. Such kits advantageously allow to determine (e.g. quantify) the miRNA levels in the sample, thereby allowing the customized formulation of the miRNA sequences, in particular the exogenous miRNA sequences, in the EVs as taught herein depending on the specific cancer targeted.

In certain embodiments, the level of expression of a miRNA or panel of miRNAs may be determined by Real Time/Quantitative reverse transcriptase polymerase chain reaction (qRT-PCR), RNA sequencing (e.g. next generation sequencing), miRNA microarray, and/or multiplex miRNA profiling assays.

In certain embodiments, the kit of parts comprises means for determining the level of expression of a panel of miRNAs comprising miR-16-5p, miR-23a-5p, miR-125b-5p, miR-145-5p, miR-146a-3p, miR-181c-5p, miR-218-5p, miR-495-3p, let-7b-5p, miR-30a-5p, miR-30b-5p, miR-30c-5p, miR-30d-5p, miR-30e-5p, miR-194-5p, miR-302a-3p, miR-302a-5p, miR-335-3p, miR-335-5p, miR-367-3p, miR-373-3p, and miR-885-5p, in a sample from a patient, preferably a human subject. In certain embodiments, the kit comprises primers capable of specifically binding miR-16-5p, miR-23a-5p, miR-125b-5p, miR-145-5p, miR-146a-3p, miR-181c-5p, miR-218-5p, miR-495-3p, let-7b-5p, miR-30a-5p, miR-30b-5p, miR-30c-5p, miR-30d-5p, miR-30e-

5p, miR-194-5p, miR-302a-3p, miR-302a-5p, miR-335-3p, miR-335-5p, miR-367-3p, miR-373-3p, and miR-885-5p.

In certain embodiments, the kit of parts comprises means for determining the level of expression of a set of oncoproteins selected from the group consisting of Protein argonaute-2, Proto-oncogene c-Akt, Annexin A3, Amyloid-beta A4 protein, Apoptosis regulator Bcl-2, Bcl-2-associated transcription factor 1, Bcl-2-like protein 2, Baculoviral IAP repeat-containing protein 5, Bone morphogenetic protein 1, cancer susceptibility candidate 7, G1/S-specific cyclin-D1, CD44 antigen, Cadherin-2, Cadherin-11, Cyclin-dependent kinase 2, Cyclin-dependent kinase inhibitor p27, CCAAT/enhancer-binding protein alpha, Cytochrome c oxidase subunit 2, Catenin beta-1, C—X—C chemokine receptor type 4, Dickkopf-related protein 1, Epidermal growth factor receptor, Fatty acid synthase, High mobility group protein HMGI-C, Insulin-like growth factor 1 receptor, Insulin-like growth factor 2 mRNA-binding protein 2, Transcription factor AP-1, Mitogen-activated protein kinase kinase kinase kinase 4, Induced myeloid leukemia cell differentiation protein Mcl-1, DNA replication licensing factor MCM5, E3 ubiquitin-protein ligase Mdm2, 72 kDa type IV collagenase, Matrix metalloproteinase-9, Metastasis-associated protein MTA3, Mucin-13, Nuclear factor NF-kappa-B p105 subunit, Phosphatidylinositol 4,5-bisphosphate 3-kinase catalytic subunit alpha isoform, Urokinase plasminogen activator surface receptor, Tumor necrosis factor ligand superfamily member 11, Ras GTPase-activating protein 1, Roundabout homolog 1, Slit homolog 2 protein, Zinc finger protein SNAI2, Mothers against decapentaplegic homolog 3, Zinc finger protein SNAIL Transcription factor SOX-2-OT, Transcription factor Sp1, TGF-beta receptor type-2, Transforming growth factor beta-1, Vascular endothelial growth factor A, and Proto-oncogene Wnt-1. For instance, the kit of parts may comprise means for determining the level of expression of a set of five oncoproteins selected from Table 1 and including LCP-1.

The terms "sample" or "biological sample" as used herein include any biological specimen obtained from a subject.

Samples may include biopsies, liquid biopsies (blood, urine, saliva, other body fluids) and tissue samples, tissue homogenates and the like. Samples may also include, without limitation, fine needle aspirate and cell lysates. Preferably, the sample is a biopsy, tissue sample, or fine needle aspirate, more preferably, the sample is a biopsy. Preferably the sample is readily obtainable by surgical methods or by minimally invasive methods, allowing the removal or isolation of said sample from the subject.

A further aspect relates to the use of the kit as defined herein for determining the level of expression of the miRNAs (present in the panel) in a sample from a patient, preferably as taught herein suitable for administration to the patient. Depending on the level of expression of the miRNAs, the panel of miRNAs and/or EVs may be customized for therapy of the patient.

TABLE 3

The endogenous miRNAs enclosed in the engineered EVmiR ™ and their target genes/proteins
Endogenous miRNAs

| EV microRNA | Target Gene | Result in Cancer |
|---|---|---|
| miR-16-5p | ↓BCL2 | Tumor suppression, increases cancer cell apoptosis in breast, prostate, lung, uterine, oral, bladder, colorectal, head and neck cancers and osteosarcoma, lymphomas and leukemia |
| | ↓FASN | Inhibition of cell proliferation and metastatic state in breast, prostate, colorectal, bladder and lung cancer |

TABLE 3-continued

The endogenous miRNAs enclosed in the engineered EVmiR ™ and their target genes/proteins
Endogenous miRNAs

| EV microRNA | Target Gene | Result in Cancer |
|---|---|---|
| | ↓SMAD3 | Suppresses epithelial-mesenchymal transition (EMT), suppresses cancer metastasis in lung cancer (bone metastasis), gastric and liver cancers, breast cancer (brain metastasis) |
| | ↓LCP1 | Suppresses invasion and metastasis of cancer cells (prostate, breast, lung, bladder, liver, melanoma, colon, leukemia, and ovarian cancer etc.), the expression predicts tumor recurrence |
| miR-23a-5p | ↓SMAD3, ↓PAK6, ↓EGR3, ↓RUNX2, ↓CXCL12, ↓BCL2 | Results in a reversal of the EMT, suppresses the migration and invasion of prostate cancer cells, counteracts the migration and invasion of lung cancer cells, leads to the retarded migration and invasion of tumor cells in osteosarcoma, increases cancer cell apoptosis |
| miR-125b-5p | ↓MCL1 | Suppresses EMT process, metastatic spread and chemoresistance in lung cancer, leukemia, pancreatic cancer, head and neck cancer, urothelial cancer, testicular cancer, breast cancer, cervical cancer |
| miR-145-5p | ↓MUC13 | Suppresses cancer cell survival in colorectal, ovarian, gastric and renal cancers |
| | ↓LCP1 | Suppresses invasion and metastasis of cancer cells (prostate, breast, lung, bladder, liver, melanoma, colon, leukemia, and ovarian cancer etc.), the expression predicts tumor recurrence |
| miR-146a-3p | ↓VEGF | Inhibits cell proliferation, metastasis and cancer-related angiogenesis and enhances cell apoptosis in renal, colorectal, lung, liver, stomach, prostate, bladder cancers and osteosarcoma and neuroblastomas. |
| miR-181c-5p | ↓PI3K | Induces cancer cell apoptosis and inhibits tumor angiogenesis in liver, pancreatic, colorectal, stomach urothelial, ovarian cancers and lymphomas and melanomas. |
| miR-218-5p | ↓SLIT2/ ROBO1 | Inhibits axon-related metastasis, distant migration of cancer cells, cancer cell invasiveness, cell growth and tumor progression in prostate, ovarian, gastric, liver, pancreatic, thyroid, breast, head and neck cancers |
| | ↓LCP1 | Suppresses invasion and metastasis of cancer cells (prostate, breast, lung, bladder, liver, melanoma, colon, leukemia, and ovarian cancer etc.), the expression predicts tumor recurrence |
| miR-495-3p | ↓ANXA3 | Inhibits the proliferation, invasion and metastasis of cancer cells in thyroid, breast, liver, prostate, testicular, renal, endometrial and pancreatic cancers |
| | ↓AKT1 | Inhibits EMT transition and metastatic disease in breast, lung, prostate and pancreatic disease |
| | ↓LCP1 | Suppresses invasion and metastasis of cancer cells (prostate, breast, lung, bladder, liver, melanoma, colon, leukemia, and ovarian cancer etc.), the expression predicts tumor recurrence |
| let-7b-5p | ↓IGF2BP2 | Suppresses cancer cell proliferation, invasion and tumor growth in Cholangiocarcinoma, thyroid, pancreatic, stomach and testicular cancer |
| | ↓HMGA2 | Inhibits EMT process, cancer aggressiveness and proliferation in multiple myeloma, osteosarcoma, thyroid, lung and colorectal cancers |

TABLE 4

The exogenous miRNAs overexpressed in the engineered EVmiR ™ and their target genes/proteins
Exogenous miRNAs

| EV microRNA | Target Gene | Result in Cancer |
|---|---|---|
| miR-30a-5p | ↓SNAI1 | Inhibits cancer cell movement and survival/Reduces cancer cell aggressiveness and spreading/Inhibits recurrence of breast and ovarian cancer |
| | ↓COX2 | Inhibits tumor promotion and tumor invasion/Increases cell death/Colorectal, pancreatic, breast, lung and hematological cancers |
| | ↓LCP1 | Suppresses invasion and metastasis of cancer cells (prostate, breast, lung, bladder, liver, melanoma, colon, leukemia, and ovarian cancer etc.), the expression predicts tumor recurrence |
| | ↓BCL2 | Tumor suppression, increases cancer cell apoptosis in breast, prostate, lung, uterine, oral, bladder, colorectal, head and neck cancers and osteosarcoma, lymphomas and leukemia |
| miR-30b-5p | ↓LCP1 | Suppresses invasion and metastasis of cancer cells (prostate, breast, lung, bladder, liver, melanoma, colon, leukemia, and ovarian cancer etc.), the expression predicts tumor recurrence |
| miR-30c-5p | ↓LCP1 | Suppresses invasion and metastasis of cancer cells (prostate, breast, lung, bladder, liver, melanoma, colon, leukemia, and ovarian cancer etc.), the expression predicts tumor recurrence |
| miR-30d-5p | ↓LCP1 | Suppresses invasion and metastasis of cancer cells (prostate, breast, lung, bladder, liver, melanoma, colon, leukemia, and ovarian cancer etc.), the expression predicts tumor recurrence |
| miR-30e-5p | ↓LCP1 | Suppresses invasion and metastasis of cancer cells (prostate, breast, lung, bladder, liver, melanoma, colon, leukemia, and ovarian cancer etc.), the expression predicts tumor recurrence |
| miR-194-5p | ↓RAB23/BCLAF1 | Inhibits cancer cell migration and chemoresistance in prostate, breast, ovarian, thyroid cancer and hepatocellular carcinomas and several gliomas |
| | ↓IGF1R | Inhibits cancer cell growth and promotes apoptosis in thyroid, colorectal, prostate, stomach, liver and ovarian cancers and some gliomas |
| | ↓SOX2OT | Inhibits cancer cell proliferation, migration and invasion in several gliomas, head and neck cancer, lung, liver and testicular cancer |
| | ↓MAP4K4/JUN/MDM2 | Inhibits cancer cell proliferation in colorectal, testicular, cervical, endometrial and liver cancer, some lymphomas and gliomas |
| | ↓BMP1 | Suppresses metastasis and cancer aggressiveness in NSCL, gastric, colon, cervical and urothelial cancers |
| | ↓p27 | Inhibits cancer cell proliferation and promotes apoptosis in NSCL, colorectal, urothelial, liver and testicular cancers and some cases of glioma and melanoma |
| miR-302a-3p | ↓CXCR4 | Inhibits invasive ability and metastasis of cancer cells in breast, ovarian, colorectal, bladder and pancreatic cancers and in some types of leukemia and uveal melanoma |
| | ↓EGFR | Suppresses metastasis and cancer cell division in breast, lung, NSCL, gastric, and some cases of glioma |

TABLE 4-continued

The exogenous miRNAs overexpressed in the engineered EVmiR ™ and their target genes/proteins
Exogenous miRNAs

| EV microRNA | Target Gene | Result in Cancer |
|---|---|---|
|  | ↓CCND1 | Inhibits tumorigenesis and cancer cell growth in head and neck, renal, prostate, breast and liver cancer and few cases of melanoma |
| miR-302a-5p | ↓HMGA2 | Inhibits proliferation, invasion and migration of cancer cells/Inhibits EMT process, cancer aggressiveness and proliferation in multiple myeloma, osteosarcoma, thyroid, lung and colorectal cancers |
|  | ↓SNAIL/SLUG/CDH2/MMP2/MMP9 (in combination with miR-367-3p) | Tumor suppressor/promotes apoptosis and cell cycle arrest of cancer cells in colorectal, prostate, renal, thyroid |
| miR-335-3p | ↓IGF1R | Inhibits tumor re-initiation in bone cancer/Inhibits cancer cell growth and promotes apoptosis in thyroid, colorectal, prostate, stomach, liver and ovarian cancers and some gliomas |
|  | ↓LCP1 | Suppresses invasion and metastasis of cancer cells (prostate, breast, lung, bladder, liver, melanoma, colon, leukemia, and ovarian cancer etc.), the expression predicts tumor recurrence |
| miR-335-5p | ↓DKK1 | Inhibits cancer cell proliferation and invasion in epithelial ovarian carcinoma, lung and bone metastasis in breast cancer, in hepatocellular carcinoma and head and neck cancer |
|  | ↓IGF1R/RANKL | Inhibits bone metastasis/Inhibits cancer cell growth and promotes apoptosis in thyroid, colorectal, prostate, stomach, liver and ovarian cancers and some gliomas |
|  | ↓CDH11 | Inhibits calcium-dependent cell-cell adhesion in gastric, breast, thyroid and testicular cancer |
|  | ↓PLAUR | Inhibits invasion and metastasis in gastric and lung cancer |
|  | ↓BCLW/SP1 | Suppressor of metastasis and cancer cell proliferation in gastric, lung, bladder, pancreatic and ovarian cancer and some cases of melanoma |
|  | ↓RASA1 | Inhibits cancer cell invasion in liver, thyroid, prostate and cervical cancer/Inhibits melanoma tumorigenesis |
|  | ↓BIRC5 | Regulates cancer cell growth and apoptosis/Promotes cancer cell death in colorectal, breast, bladder, skin, lung, thyroid cancer and neuroblastoma |
| miR-367-3p | ↓HMGA2 | Inhibits tumor metastasis in endometrial cancer/Inhibits EMT process, cancer aggressiveness and proliferation in multiple myeloma, osteosarcoma, thyroid, lung and colorectal cancers |
|  | ↓CEBPA | Tumor regression in glioma, myeloid leukemia and liver cancer |
|  | ↓MTA3 | Inhibits cancer cell proliferation, migration, invasion and metastasis in lung, breast, pancreatic cancers |
|  | ↓RAB23 | Inhibits cancer cell migration and chemoresistance in prostate, breast, ovarian, thyroid cancer and hepatocellular carcinomas and several gliomas |
| miR-373-3p | ↓MMP2/MMP9 | Tumor suppressor/promotes apoptosis and cell cycle arrest of cancer cells in colorectal, prostate, renal, thyroid cancers |
|  | ↓CD44/TGFBR2 | Tumor suppressor in colorectal, lung, stomach and breast cancer |

TABLE 4-continued

The exogenous miRNAs overexpressed in the engineered
EVmiR ™ and their target genes/proteins
Exogenous miRNAs

| EV microRNA | Target Gene | Result in Cancer |
|---|---|---|
| | ↓APP | Inhibits proliferation of cancer cells in lung adenocarcinoma, colorectal, testicular and ovarian cancers |
| | ↓NFKB1/TGFB1 | Inhibits tumor progression, metastasis and inflammation in breast, ovarian, colorectal and head and neck cancer and lymphoma |
| miR-885-5p | ↓LCP1 | Suppresses invasion and metastasis of cancer cells (prostate, breast, lung, bladder, liver, melanoma, colon, leukemia, and ovarian cancer etc.), the expression predicts tumor recurrence |
| | ↓CDK2 | Inhibits hyperproliferation/induces apoptosis in malignant cells in breast, oral, colorectal, cervical, ovarian cancer and lymphoma |
| | ↓MCM5 | Inhibits cancer cell proliferation in thyroid, cervical, bladder, esophageal, gastric and prostate cancer |
| | ↓WNT/CTNNB1 | Inhibit metastatic processes/reduces CSC sternness/reduces cancer state aggressiveness in most cancer types |
| | ↓CASC7/AGO2 | Inhibits cancer cell proliferation and survival in colorectal, breast, cervical, pancreatic, head and neck, thyroid, prostate, stomach cancer and most gliomas |

The present application also provides aspects and embodiments as set forth in the following Statements:

1. A method of treating LCP-1 positive cancer patients via administration of specific miRNA sequences (including miR-885-5p). MiRNA sequences may be embedded within delivery vehicles that have been loaded with or overexpress specific miRNA sequences (including EVmiR™ complexes) and which have been found to affect cancer related proteins that have been linked to cancer growth and metastasis.
2. The method according to statement 1 wherein the panel of miRNAs corresponding to miR-16-5p, miR-23a-5p, miR-125b-5p, miR-145-5p, miR-146a-3p, miR-181c-5p, miR-218-5p, miR-495-3p, let-7b-5p, miR-30a-5p, miR-30b-5p, miR-30c-5p, miR-30d-5p, miR-30e-5p, miR-194-5p, miR-302a-3p, miR-302a-5p, miR-335-3p, miR-335-5p, miR-367-3p, miR-373-3p and miR-885-5p (see miRNA Panel, Table 1).
3. The method according to statement 1 where the delivery vehicle is an extracellular vesicle (EV) or a microvesicle derived from stem cells of the umbilical cord (including Wharton's Jelly cells), blood, cord blood or bone marrow and where the stem cells may be of mesenchymal origin or progenitor origin.
4. The method defined in statement 3, wherein EVs are produced from stem cells in a narrow size range (30 to 300 nm) and are characterized by specific intracellular and cell membrane proteins (including P-selectin, Integrin beta-1, Vascular cell adhesion protein 1, Annexins, Tumor susceptibility gene 101 protein, Hsp70-binding protein 1, CD9, CD29, CD63, CD73, CD81, CD90) and by specific endogenous miRNA sequences (see Table 2).
5. The method defined in statement 1, wherein the EVs are loaded with specific miRNA sequences targeted against cancer disease (see Table 3 and Table 4).
6. The method defined in statement 2, wherein the specific miRNA sequences are selected from the panel comprising of miR-16-5p, miR-23a-5p, miR-125b-5p, miR-145-5p, miR-146a-3p, miR-181c-5p, miR-218-5p, miR-495-3p, let-7b-5p, miR-30a-5p, miR-30b-5p, miR-30c-5p, miR-30d-5p, miR-30e-5p, miR-194-5p, miR-302a-3p, miR-302a-5p, miR-335-3p, miR-335-5p, miR-367-3p, miR-373-3p and miR-885-5p, according to cancer type and disease staging based on the diagnostic profiling of patients (see Table 3 and Table 4).
7. The method defined in statement 1, wherein the specific miRNA sequences are either (i) preloaded in the EVs following specific upregulation in the parent stem cell via transfection or de novo induction or (ii) loaded in the already formed EVs via direct transfer/chemical insertion/electroporation (see Section of Methods).
8. The method defined in statement 1, wherein the specific proteins targeted and which are overexpressed in cancer cells, are Protein argonaute-2, Proto-oncogene c-Akt, Annexin A3, Amyloid-beta A4 protein, Apoptosis regulator Bcl-2, Bcl-2-associated transcription factor 1, Bcl-2-like protein 2, Baculoviral IAP repeat-containing protein 5, Bone morphogenetic protein 1, cancer susceptibility candidate 7, Gl/S-specific cyclin-D1, CD44 antigen, Cadherin-2, Cadherin-11, Cyclin-dependent kinase 2, Cyclin-dependent kinase inhibitor p27, CCAAT/enhancer-binding protein alpha, Cytochrome c oxidase subunit 2, Catenin beta-1, C—X—C chemokine receptor type 4, Dickkopf-related protein 1, Epidermal growth factor receptor, Fatty acid synthase, High mobility group protein HMGI-C, Insulin-like growth factor 1 receptor, Insulin-like growth factor 2 mRNA-binding protein 2, Transcription factor AP-1, Mitogen-activated protein kinase kinase kinase kinase 4, Induced myeloid leukemia cell differentiation protein Mcl-1, DNA replication licensing factor MCM5, E3 ubiquitin-protein ligase Mdm2, 72 kDa type IV collagenase, Matrix metalloproteinase-9, Metastasis-associated protein MTA3, Mucin-13, Nuclear factor NF-kappa-B p105 subunit, Phosphatidylinositol 4,5-bisphosphate 3-kinase catalytic subunit alpha isoform, Urokinase plasminogen activator surface receptor, Tumor necrosis factor ligand superfamily member 11, Ras GTPase-activating protein 1, Roundabout homolog 1, Slit homolog 2 protein, Zinc finger protein SNAI2, Mothers against decapentaplegic homolog 3, Zinc finger protein SNAIL Transcription factor SOX-2-OT, Transcription factor Sp1, TGF-beta receptor type-2, Transforming growth factor beta-1, Vascular endothelial growth factor A, Proto-oncogene Wnt-1 (see Table 2), but not limited to, as individual miRNA have multiple targets.

9. The method defined in statement 1, wherein the cancer types targeted are the ones that have been shown to overexpress LCP-1 as well as members of the protein panel defined in statement 8 and include cancer types such as skin melanoma, uveal melanoma, glioma, breast cancer, head and neck cancer, oral cancer, thyroid cancer, lung cancer, liver cancer, pancreatic cancer, stomach cancer, colorectal cancer, bladder cancer, urothelial cancer, renal cancer, kidney cancer, bone cancer, prostate cancer, testicular cancer, cervical cancer, ovarian cancer and endometrial cancer as well as any other cancer types that overexpress the oncoproteins defined in statement 8 above.

10. The method defined in statement 1, wherein cancer patients are selected for administration of the miRNA-loaded EVs via a specific diagnostic kit designed to select for LCP-1 positive and/or LCP-1 phosphorylation state, miR-885-5p negative tumors and miR-885-5p expression in tissue and liquid biopsies and biofluids, as well as a combination of the miRNAs and proteins defined in statements 6 and 8 above.

11. The method defined in statement 1, wherein the miRNA-loaded EVs are administered in cancer patients either locally or systemically in liquid or solid form either orally, intramuscularly or intravenously.

12. The method defined in statement 1, wherein the miRNA-loaded EVs can be administered prophylactically or therapeutically as the primary therapeutic approach or in combination with other therapies (such as chemotherapy, radiation therapy and other biological therapies).

13. The method defined in statement 1, wherein the miRNA-loaded EVs migrate to the tumor sites (both primary and metastatic) including sites in the brain (by crossing the blood-brain barrier).

14. The method defined in statement 1, wherein the miRNA-loaded EVs fuse with the cell membrane of cancer cells and release the therapeutic miRNAs in the target cell cytoplasm.

15. The method defined in statement 1, wherein the extracellular vesicles derived from stem cells and/or mesenchymal stem cells are replaced with/substituted by/enveloped in other biological or synthetic vesicles and materials (such as liposomes, collagen, PEG and nano/microparticles) and which are loaded with the specific miRNA sequences (including miR-885-5p) targeted against the LCP-1 protein in tumors.

16. A panel of miRNAs comprising miR-16-5p, miR-23a-5p, miR-125b-5p, miR-145-5p, miR-146a-3p, miR-181c-5p, miR-218-5p, miR-495-3p, and let-7b-5p, and further comprising one or more miRNAs selected from the group consisting of miR-30a-5p, miR-30b-5p, miR-30c-5p, miR-30d-5p, 24 of 33 10764-08918 US miR-30e-5p, miR-194-5p, miR-302a-3p, miR-302a-5p, miR-335-3p, miR-335-5p, miR-367-3p, miR-373-3p, and miR-885-5p.

17. The panel according to statement 16, wherein the panel comprises miR-16-5p, miR-23a-5p, miR-125b-5p, miR-145-5p, miR-146a-3p, miR-181c-5p, miR-218-5p, miR-495-3p, let-7b-5p, and miR-885-5p.

18. The panel according to statement 16 or 17, wherein the panel comprises miR-16-5p, miR-23a-5p, miR-125b-5p, miR-145-5p, miR-146a-3p, miR-181c-5p, miR-218-5p, miR-495-3p, let-7b-5p, miR-30a-5p, miR-30b-5p, miR-30c-5p, miR-30d-5p, miR-30e-5p, miR-194-5p, miR-302a-3p, miR-302a-5p, miR-335-3p, miR-335-5p, miR-367-3p, miR-373-3p, and miR-885-5p.

19. The panel according to any one of statements 16 to 18, wherein the panel comprises naturally occurring miRNAs and synthetically overexpressed miRNAs, wherein the synthetically overexpressed miRNAs are synthetic premiRs, mature miRs, antimiRs or de novo induced miRs.

20. The panel according to any one of statements 16 to 19, wherein the panel is embedded within an extracellular vesicle (EV) or other biological or synthetic vesicle or material, such as liposomes, collagen, PEG, a nanoparticle or a microparticle.

21. An extracellular vesicle (EV) loaded with the panel of miRNAs as defined in any one of statements 16 to 19 or with nucleic acid encoding the panel of miRNAs as defined in any one of statements 16 to 19.

22. The extracellular vesicles (EVs) according to statement 21, wherein the EVs are derived from stem cells sourced from umbilical cord, Wharton's Jelly, blood, cord blood or bone marrow, wherein the stem cells are of mesenchymal origin or progenitor origin.

23. The EVs according to statement 21 or 22, wherein the EVs are produced in a size range of 10 nm to 500 nm or 30 nm to 300 nm.

24. The EVs according to any one of statements 21 to 23, wherein the EVs are characterized by intracellular and cell membrane proteins comprising P-selectin, Integrin beta-1, Vascular cell adhesion protein 1, Annexins, Tumor susceptibility gene 101 protein, Hsp70-binding protein, CD9, CD29, CD63, CD73, CD81, and CD90.

25. The EVs according to any one of statements 21 to 24, wherein the miRNA sequences are (i) preloaded in the EVs following upregulation in the parent stem cell via transfection or de novo induction, and/or (ii) loaded in the already formed EVs via direct transfer, chemical insertion and/or electroporation.

26. The panel according to any one of statements 16 to 20, or the EVs according to any one of statements 21 to 25, for use in a method of treating LCP-1 positive cancer in a patient.

27. The panel for use according to statement 26, or the EVs for use according to statement 26, wherein the one or more miRNAs selected from the group consisting of miR-30a-5p, miR-30b-5p, miR-30c-5p, miR-30d-5p, miR-30e-5p, miR-194-5p, miR-302a-3p, miR-302a-5p, miR-335-3p, miR-335-5p, miR-367-3p, miR-373-3p, and miR-885-5p are chosen according to cancer type and disease staging based on diagnostic profiling of patients.

28. The panel for use according to statement 26 or 27, or the EVs for use according to statement 26 or 27, wherein the LCP-1 positive cancer cells overexpress any one or more proteins selected from the group consisting of Protein argonaute-2, Proto-oncogene c-Akt, Annexin A3, Amyloid-beta A4 protein, Apoptosis regulator Bcl-2, Bcl-2-associated transcription factor 1, Bcl-2-like protein 2, Baculoviral IAP repeat-containing protein 5, Bone morphogenetic protein 1, cancer susceptibility candidate 7, Gl/S-specific cyclin-D1, CD44 antigen, Cadherin-2, Cadherin-11, Cyclin-dependent kinase 2, Cyclin-dependent kinase inhibitor p27, CCAAT/enhancer-binding protein alpha, Cytochrome c oxidase subunit 2, Catenin beta-1, C—X—C chemokine receptor type 4, Dickkopf-related protein 1, Epidermal growth factor receptor, Fatty acid synthase, High mobility group protein HMGI-C, Insulin-like growth factor 1 receptor, Insulin-like growth factor 2 mRNA-binding protein 2, Transcription factor AP-1, Mitogen-activated protein kinase kinase kinase kinase 4, Induced myeloid leukemia cell differentiation protein Mcl-1, DNA replication licensing factor MCM5, E3 ubiquitin-protein ligase Mdm2, 72 kDa type IV collagenase, Matrix metalloproteinase-9, Metastasis-associated protein MTA3, Mucin-13, Nuclear factor NF-kappa-B p105 subunit, Phosphatidylinositol 4,5-bisphosphate 3-kinase catalytic subunit alpha isoform, Urokinase plasminogen activator surface receptor, Tumor necrosis factor ligand superfamily member 11, Ras GTPase-activating protein 1, Roundabout homolog 1, Slit homolog 2 protein, Zinc finger protein SNAI2, Mothers against decapentaplegic homolog 3, Zinc finger protein SNAIL Transcription factor SOX-2-OT, Transcription factor Sp1, TGF-beta receptor type-2, Transforming growth factor beta-1, Vascular endothelial growth factor A, and Proto-oncogene Wnt-1.

29. The panel for use according to any one of statements 26 to 28, or the EVs for use according to any one of statements 26 to 28, wherein the LCP-1 positive cancer is selected from the group consisting of breast cancer, skin melanoma, uveal melanoma, glioma, head and neck cancer, oral cancer, thyroid cancer, lung cancer, liver cancer, pancreatic cancer, stomach cancer, colorectal cancer, bladder cancer, urothelial cancer, renal cancer, kidney cancer, bone cancer, prostate cancer, testicular cancer, cervical cancer, ovarian cancer, endometrial cancer, and any other cancer type that overexpresses one or more oncoproteins as defined in statement 28.

30. The panel for use according to any one of statements 26 to 29, or the EVs for use according to any one of statements 26 to 29, wherein cancer patient is selected for administration of the panel or the miRNA-loaded EVs via a diagnostic kit designed to select for any one or more of LCP-1 positive tumors, LCP-1 phosphorylation state, miR-885-5p negative tumors, miR-885-5p expression, and expression of a combination of the miRNAs and proteins defined in statement 28, in tissue, liquid biopsies, or biofluids.

31. The panel for use according to any one of statements 26 to 30, or the EVs for use according to any one of statements 26 to 30, wherein the miRNA-loaded EVs are administered in cancer patients either locally or systemically, in liquid or solid form, either orally, intramuscularly or intravenously.

32. The panel for use according to any one of statements 26 to 31, or the EVs for use according to any one of statements 26 to 31, wherein the miRNA-loaded EVs can be administered prophylactically or therapeutically as the primary therapeutic approach or in combination with other therapies such as chemotherapy, radiation therapy or other biological therapies.

33. The panel for use according to any one of statements 26 to 32, or the EVs for use according to any one of statements 26 to 32, wherein the miRNA-loaded EVs migrate to the tumor sites such as to tumor sites in the brain.

34. The panel for use according to statement 33, or the EVs for use according to statement 33, wherein the tumor sites are primary or metastatic tumor sites.

35. The panel for use according to any one of statements 26 to 34, or the EVs for use according to any one of statements 26 to 34, wherein the miRNA-loaded EVs fuse with the cell membrane of cancer cells and release the therapeutic miRNAs in the target cell cytoplasm.

36. A kit of parts comprising means for determining the level of expression of a panel of miRNAs comprising miR-30a-5p, miR-30b-5p, miR-30c-5p, miR-30d-5p, miR-30e-5p, miR-194-5p, miR-302a-3p, miR-302a-5p, miR-335-3p, miR-335-5p, miR-367-3p, miR-373-3p, and miR-885-5p, in a sample from a patient.

37. The kit of parts according to statement 36, wherein the kit of parts comprises means for determining the level of expression of a panel of miRNAs comprising miR-16-5p, miR-23a-5p, miR-125b-5p, miR-145-5p, miR-146a-3p, miR-181c-5p, miR-218-5p, miR-495-3p, let-7b-5p, miR-30a-5p, miR-30b-5p, miR-30c-5p, miR-30d-5p, miR-30e-5p, miR-194-5p, miR-302a-3p, miR-302a-5p, miR-335-3p, miR-335-5p, miR-367-3p, miR-373-3p, and miR-885-5p, in a sample from a patient.

38. Use of a kit of parts as defined in statements 36 or 37 for determining the level of expression of the miRNAs in a sample from a patient, preferably for preparing EVs as defined in any one of statements 21 to 25 for administration to the patient.

EXAMPLES

Figure 3:
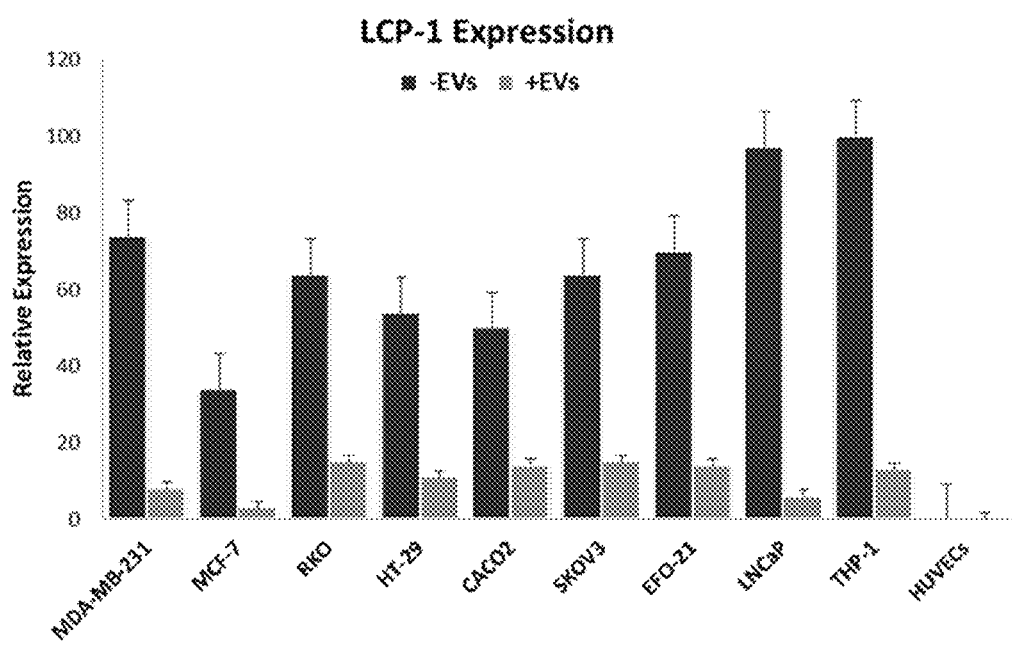
FIG. 3. Assessing the expression levels of protein LCP-1. The concentration of the LCP-1 was tested in a range of control and cancer cell lines before and after the treatment with EVmiR™ loaded with the miR-885-5p by using quantitative western blot assays.
Figure 4:
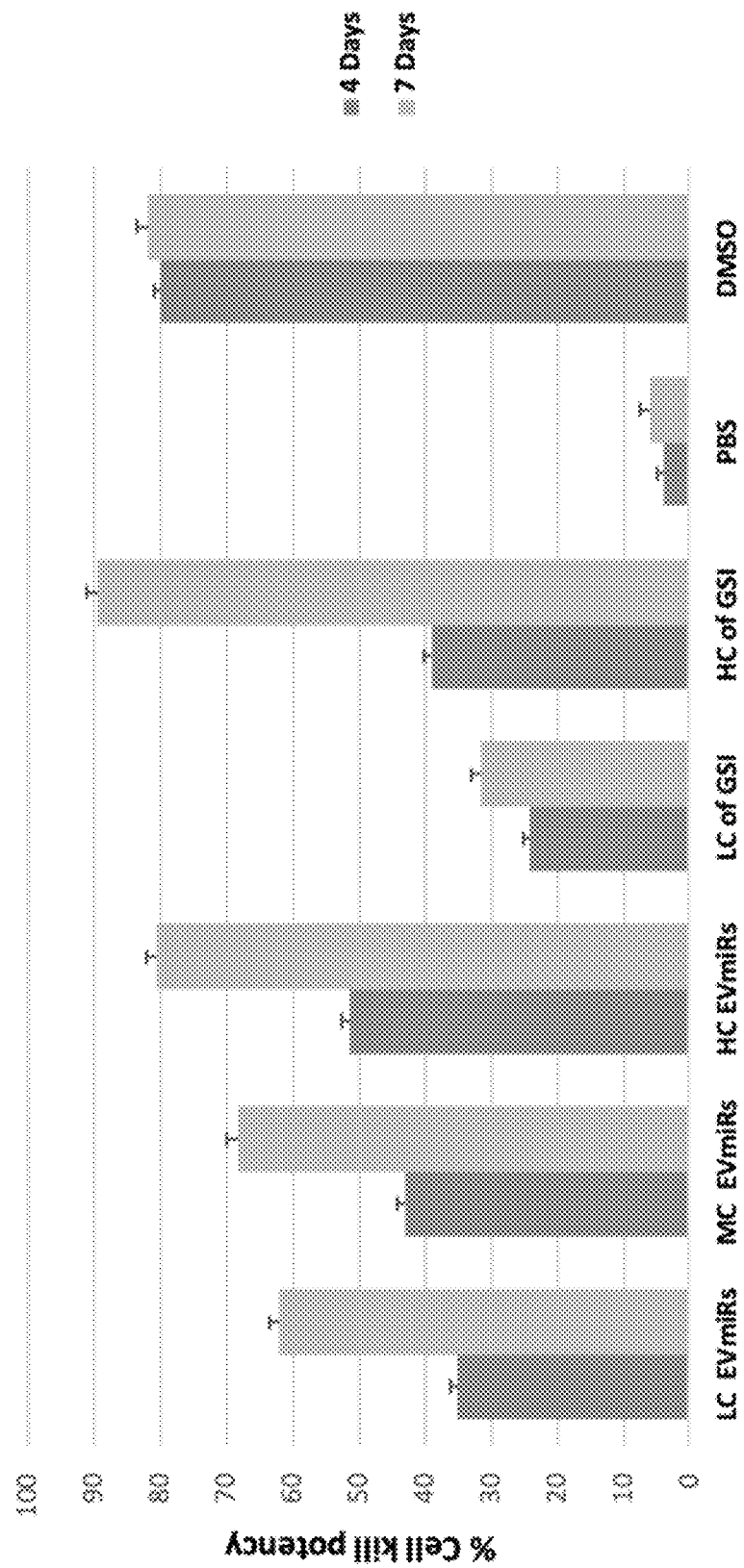
FIG. 4. Cell proliferation assay on breast cancer cell MDA-MB-231. Cell proliferation assay on MDA-MB-231 breast cancer in the presence of EVmiRs (LC: low concentration, MC: medium concentration and HC: high concentration), GSI inhibitor and DMSO as known cytotoxic factors as controls, and PBS/normal conditioned media as internal controls; cell treatment for 4 and 7 days.

In vitro study to assess cancer cell response to EV-mediated miRNA therapy: Breast (MDA-MB-231 & MCF-7), colon (RKO, HT-29, CACO2) and ovarian (SKOV3, EFO-21) adenocarcinoma, prostate carcinoma (LNCaP) and acute monocytic leukemia (THP-1) cell lines were exposed to EVs containing the exogenous therapeutic miR-885-5p (as well as the endogenous panel of miRNAs, see Table 2). The response to treatment was evaluated by cell morphology, proliferation, migration, gene expression and apoptosis assays (FIGS. 3 and 4). Our in vitro experiments confirmed that stem cell-derived EVs are internalized by the various cancer cell lines and induce a biological effect as evidenced by membrane damage, cell shrinkage and blebbing in the targeted cells (FIG. 5). Significantly, there was evidence that EVs induce apoptosis, inhibit cell proliferation and attenuate tumor growth and metastasis in a dose/time-dependent manner. The pro-apoptotic and anti-migrating effects of EVs in cancer cells were almost completely abrogated by RNase treatment of the EVs before introduction to cell cultures. A range of EVs with different sizes were tested in vitro, as well as in vivo (FIG. 6) and in silico in order to achieve maximum delivery efficiency through experimental and modelling investigation of the size-dependent EV kinetics and biodistribution (particle analysis using SEC and TRPS). FIG. 6 shows co-localization of EVmiRs with the cancer cells at the tumor site at different time points (FIGS. 6A and 6B). EVmiRs were thus able to specifically target and attack cancer cells in vivo.

FIG. 7 shows in the left-handed insert a scanning electron micrograph of EVmiRs. The larger image shows EVmiRs attacking the MDA-MB-231 cell line. It is illustrated that EVmiRs co-localize with the tumor cells and load their contents though membrane uptake mechanisms.

In vivo cancer models to evaluate response to EVmiR™ based therapy: With our invention, we have developed a novel miRNA-based therapeutic agent that targets and suppresses LCP1 in both primary and metastatic tumors. In our in vivo studies of metastatic breast (breast-to-brain distant metastasis) and colorectal cancer we were able to monitor and quantify fluorescently labelled EVs in circulation and to image their biodistribution and incorporation in cells and organs in both healthy and tumor-bearing mice. We have discovered that the therapeutic EVmiR™ complexes accumulate at sites of tumor growth, both primary and metastatic, including the brain (i.e. EVs are able to cross the blood-brain barrier). We then investigated the therapeutic potential of the EVmiR™ system in animal cancer models by administering the engineered EVs containing specific therapeutic miRNAs (selected from Table 4) in tumor-bearing mice and monitoring them in real time using in vivo imaging techniques. Assessment of the tumor burden via in vivo imaging demonstrated a reduction in tumor growth and metastatic load over time in mice treated with EVmiR™ compared to untreated mice. We have also identified the dose regime required to produce measurable therapeutic results and also the maximum tissue/tumor depth that the EVmiR™ complex can reach. Utilizing a mouse model of prostate cancer, we further demonstrated that reduced expression of LCP-1 inhibits metastasis, while increasing LCP-1 expression and phosphorylation stimulates metastasis of primary tumors.

Mode of action of therapeutic agent (construction of signaling pathways): State-of-the-art techniques such as proteomics, tissue profiling, and miRNA-omics were performed on cells, EVs and explanted tissue from the tumor site in order to identify the pathways and mechanisms that enable the anti-cancer effect of our EVmiR™ complexes. Custom multiplex assays were employed to elucidate the signaling pathways affected by our therapeutic agent by measuring the phosphorylation activity of the LCP-1 protein at Ser5 and other related targets. Data normalization and analysis with state-of-the-art pathway optimization algorithms were utilized to pinpoint the mode of action of the therapeutic EVmiR™ complexes. Furthermore, AFM studies were carried out to characterize the mechanical properties of metastatic cancer cells following downregulation of the LCP-1 protein by EVs-containing the miR-885-5p miRNA and demonstrated the link between cell plasticity and high metastatic potential of cancer cells.

Modelling of tumor response to miRNA-based therapy: We have also utilized innovative patient-specific multiscale computational models to enable the design of more efficient EVmiR™ based therapeutic delivery systems by analyzing and predicting: 1) the vascular deposition of EVs derived from stem cells (mesenchymal or otherwise); 2) the response of tumor to EV-mediated miRNA therapy. This is an integral part of our therapeutic strategy due to the complexity of the task of developing delivery systems that are targeted to a complex tumor microenvironment, which in most cases hinders their efficient penetration and therapeutic action.

Here we describe specific embodiments/examples of the invention, however it should be understood that the invention encompasses variations and modifications that are within the scope and spirit of the invention as described in the claims below.

REFERENCES

1. Lin C S, Park T, Chen Z P, Leavitt J. Human plastin genes. comparative gene structure, chromosome location, and differential expression in normal and neoplastic cells. *J Biol Chem.* 1993; 268(4):2781-2792.
2. Lommel M J, Trairatphisan P, Gabler K, et al. L-plastin Ser5 phosphorylation in breast cancer cells and in vitro is mediated by RSK downstream of the ERK/MAPK pathway. *FASEB J.* 2016; 30(3):1218-1233.
3. Shinomiya H. Plastin family of actin-bundling proteins: Its functions in leukocytes, neurons, intestines, and cancer. *Int J Cell Biol.* 2012; 2012:213492.
4. Samstag Y, Eibert S M, Klemke M, Wabnitz G H. Actin cytoskeletal dynamics in T lymphocyte activation and migration. *J Leukoc Biol.* 2003; 73(1):30-48.
5. Wabnitz G H, Kocher T, Lohneis P, et al. Costimulation induced phosphorylation of L-plastin facilitates surface transport of the T cell activation molecules CD69 and CD25. *Eur J Immunol.* 2007; 37(3): 649-662.
6. Wang J, Chen H, Brown E J. L-plastin peptide activation of alpha(v)beta(3)-mediated adhesion requires integrin conformational change and actin filament disassembly. *J Biol Chem.* 2001; 276(17):14474-14481.
7. Freeley M, O'Dowd F, Paul T, et al. L-plastin regulates polarization and migration in chemokine-stimulated human T lymphocytes. *J Immunol.* 2012; 188(12):6357-6370.
8. Janji B, Giganti A, De Corte V, et al. Phosphorylation on Ser5 increases the F-actin-binding activity of L-plastin and promotes its targeting to sites of actin assembly in cells. *J Cell Sci.* 2006; 119(Pt 9):1947-1960.
9. Wabnitz G H, Lohneis P, Kirchgessner H, et al. Sustained LFA-1 cluster formation in the immune synapse requires the combined activities of L-plastin and calmodulin. Eur Jlmmunol. 2010; 40(9):2437-2449.
10. Pazdrak K, Young T W, Straub C, Stafford S, Kurosky A. Priming of eosinophils by GM-CSF is mediated by protein kinase Cbetal1-phosphorylated L-plastin. *J Immunol.* 2011; 186(11):6485-6496.
11. Ishida H, Jensen K V, Woodman A G, Hyndman M E, Vogel H J. The calcium-dependent switch helix of L-plastin regulates actin bundling. *Sci Rep.* 2017; 7:40662.
12. Cai X, Hagedorn C H, Cullen B R. Human microRNAs are processed from capped, polyadenylated transcripts that can also function as mRNAs. *RNA.* 2004; 10(12): 1957-1966.
13. Back D, Villen J, Shin C, Camargo F D, Gygi S P, Bartel D P. The impact of microRNAs on protein output. Nature. 2008; 455(7209):64-71.
14. Gupta G P, Massague J. Cancer metastasis: Building a framework. *Cell.* 2006; 127(4):679-695.

```
SEQUENCE LISTING
hsa-miR-16-5p:
                                            (SEQ ID NO: 1)
UAGCAGCACGUAAAUAUUGGCG hsa-miR-23a-5p (also known as hsa-miR-23a*):
                                            (SEQ ID NO: 2)
GGGGUUCCUGGGGAUGGGAUUU
```

-continued

```
hsa-miR-30a-5p (also known as hsa-miR-30a):
                                        (SEQ ID NO: 3)
UGUAAACAUCCUCGACUGGAAG hsa-miR-30b-5p (also known as hsa-miR-30b):
                                        (SEQ ID NO: 4)
UGUAAACAUCCUACACUCAGCU hsa-miR-30c-5p (also known as hsa-miR-30c):
                                        (SEQ ID NO: 5)
UGUAAACAUCCUACACUCUCAGC hsa-miR-30d-5p (also known as hsa-miR-30d):
                                        (SEQ ID NO: 6)
UGUAAACAUCCCCGACUGGAAG hsa-miR-30e-5p (also known as hsa-miR-30e):
                                        (SEQ ID NO: 7)
UGUAAACAUCCUUGACUGGAAG hsa-miR-125b-5p (also known as hsa-miR-125b):
                                        (SEQ ID NO: 8)
UCCCUGAGACCCUAACUUGUGA hsa-miR-145-5p (also known as hsa-miR-145):
                                        (SEQ ID NO: 9)
GUCCAGUUUUCCCAGGAAUCCCU hsa-miR-146a-3p (also known as hsa-miR-146*):
                                        (SEQ ID NO: 10)
CCUCUGAAAUUCAGUUCUUCAG hsa-miR-181c-5p (also known as hsa-miR-181c):
                                        (SEQ ID NO: 11)
AACAUUCAACCUGUCGGUGAGU hsa-miR-194-5p (also known as hsa-miR-194):
                                        (SEQ ID NO: 12)
UGUAACAGCAACUCCAUGUGGA hsa-miR-218-5p (also known as hsa-miR-218):
                                        (SEQ ID NO: 13)
UUGUGCUUGAUCUAACCAUGU hsa-miR-302a-3p (also known as hsa-miR-302a/
hsa-miR-302):
                                        (SEQ ID NO: 14)
UAAGUGCUUCCAUGUUUUGGUGA hsa-miR-302a-5p (also known as hsa-miR-302a*):
                                        (SEQ ID NO: 15)
ACUUAAACGUGGAUGUACUUGCU hsa-miR-335-3p (also known as hsa-miR-335*):
                                        (SEQ ID NO: 16)
UUUUUCAUUAUUGCUCCUGACC hsa-miR-335-5p (also known as hsa-miR-335):
                                        (SEQ ID NO: 17)
UCAAGAGCAAUAACGAAAAAUGU hsa-miR-367-3p (also known as hsa-miR-367):
                                        (SEQ ID NO: 18)
AAUUGCACUUUAGCAAUGGUGA hsa-miR-373-3p (also known as hsa-miR-373):
                                        (SEQ ID NO: 19)
GAAGUGCUUCGAUUUUGGGGUGU hsa-miR-495-3p (also known as hsa-miR-495):
                                        (SEQ ID NO: 20)
AAACAAACAUGGUGCACUUCUU hsa-miR-885-5p:
                                        (SEQ ID NO: 21)
UCCAUUACACUACCCUGCCUCU hsa-let-7b-5p (also known as hsa-let-7b):
                                        (SEQ ID NO: 22)
UGAGGUAGUAGGUUGUGUGGUU
```

---

The invention claimed is:

1. An extracellular vesicle (EV) loaded with a panel of miRNAs or with nucleic acid encoding the panel of miRNAs, wherein the panel of miRNAs comprises miR-16-5p, miR-23a-5p, miR-125b-5p, miR-145-5p, miR-146a-3p, miR-181c-5p, miR-218-5p, miR-495-3p, let-7b-5p, and miR-885-5p, wherein the EV is produced from a stem cell of mesenchymal origin modified to overexpress miR-885-5p as compared to a wild-type cell of the same type, wherein the EV selectively migrates to tumor tissue as compared to healthy tissue in a mammal.

2. The EV of claim 1, wherein the panel further comprises one or more miRNAs selected from the group consisting of miR-30a-5p, miR-30b-5p, miR-30c-5p, miR-30d-5p, miR-30e-5p, miR-194-5p, miR-302a-3p, miR-302a-5p, miR-335-3p, miR-335-5p, miR-367-3p, and miR-373-3p.

3. The EV of claim 1, wherein the panel comprises miR-16-5p, miR-23a-5p, miR-125b-5p, miR-145-5p, miR-146a-3p, miR-181c-5p, miR-218-5p, miR-495-3p, let-7b-5p, miR-30a-5p, miR-30b-5p, miR-30c-5p, miR-30d-5p, miR-30e-5p, miR-194-5p, miR-302a-3p, miR-302a-5p, miR-335-3p, miR-335-5p, miR-367-3p, miR-373-3p, and miR-885-5p.

4. The EV of claim 1, wherein the panel comprises naturally occurring miRNAs and synthetically overexpressed miRNAs, wherein the synthetically overexpressed miRNAs are synthetic premiRs, mature miRs, antimiRs or de novo induced miRs.

5. The EV of claim 1, wherein the stem cells are umbilical cord, Wharton's Jelly, blood, cord blood or bone marrow stem cells.

6. The EV of claim 1, wherein the EV have a size range of 10 nm to 500 nm.

7. The EV of claim 1, wherein the EV comprise P-selectin, Integrin beta-1, Vascular cell adhesion protein 1, Annexins, Tumor susceptibility gene 101 protein, Hsp70-binding protein, CD9, CD29, CD63, CD73, CD81, and CD90.

8. The EV of claim 1, wherein the expression of miR-885-5p in the stem cell of mesenchymal origin has been up upregulated via transfection or de novo induction.

9. The EV of claim 1, wherein the EV have a size range of 30 nm to 300 nm.

* * * * *